US010806950B2

(12) United States Patent
Fahrig et al.

(10) Patent No.: US 10,806,950 B2
(45) Date of Patent: Oct. 20, 2020

(54) RAPID IMAGING SYSTEMS AND METHODS FOR FACILITATING RAPID RADIATION THERAPIES

(71) Applicant: The Board of Trustees of the Leland Stanford Junior University, Stanford, CA (US)

(72) Inventors: Rebecca Fahrig, Moehrendorf (DE); Billy Wiseman Loo, Foster City, CA (US); Peter G. Maxim, Palo Alto, CA (US); Sami Tantawi, Stanford, CA (US)

(73) Assignee: The Board of Trustees of The Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/944,670

(22) Filed: Apr. 3, 2018

(65) Prior Publication Data

US 2018/0296858 A1    Oct. 18, 2018

Related U.S. Application Data

(60) Division of application No. 15/068,471, filed on Mar. 11, 2016, now Pat. No. 9,962,562, which is a
(Continued)

(51) Int. Cl.
*A61N 5/10* (2006.01)
*H05H 7/04* (2006.01)

(52) U.S. Cl.
CPC ......... *A61N 5/1084* (2013.01); *A61N 5/1039* (2013.01); *A61N 5/1043* (2013.01);
(Continued)

(58) Field of Classification Search
CPC .. A61N 5/1084; A61N 5/1043; A61N 5/1065; A61N 5/1077; A61N 5/1078; A61N 2005/1089; A61N 5/1064; A61N 5/1067
See application file for complete search history.

(56) References Cited

U.S. PATENT DOCUMENTS

| 3,757,118 A | 9/1973 | Hodge et al. |
| 4,644,168 A | 2/1987 | Rand et al. |

(Continued)

FOREIGN PATENT DOCUMENTS

| CN | 101453951 | 6/2009 |
| EP | 1358908 | 11/2003 |

(Continued)

OTHER PUBLICATIONS

U.S. Appl. No. 15/068,268, "Final Office Action", dated Mar. 21, 2019, 22 pages.
(Continued)

*Primary Examiner* — Wyatt A Stoffa
(74) *Attorney, Agent, or Firm* — Kilpatrick Townsend & Stockton LLP

(57) ABSTRACT

Methods and system for facilitating rapid radiation treatments are provided herein and relate in particular to radiation generation and delivery, beam control, treatment planning, imaging and dose verification. The methods and systems described herein are particularly advantageous when used with a compact high-gradient, very high energy electron (VHEE) accelerator and delivery system (and related processes) capable of treating patients from multiple beam directions with great speed, using all-electromagnetic or radiofrequency deflection steering is provided, that can deliver an entire dose or fraction of high-dose radiation
(Continued)

therapy sufficiently fast to freeze physiologic motion, yet with a better degree of dose conformity or sculpting than conventional photon therapy.

28 Claims, 18 Drawing Sheets

Related U.S. Application Data continuation of application No. PCT/US2014/055270, filed on Sep. 11, 2014.

(60) Provisional application No. 61/876,679, filed on Sep. 11, 2013.

(52) U.S. Cl.
CPC ......... *A61N 5/1064* (2013.01); *A61N 5/1067* (2013.01); *A61N 5/1077* (2013.01); *A61N 5/1078* (2013.01); *A61N 5/1081* (2013.01); *A61N 2005/1055* (2013.01); *A61N 2005/1058* (2013.01); *A61N 2005/1076* (2013.01); *A61N 2005/1089* (2013.01); *A61N 2005/1091* (2013.01); *A61N 2005/1098* (2013.01); *H05H 2007/048* (2013.01)

(56) References Cited

U.S. PATENT DOCUMENTS

| | | | |
|---|---|---|---|
| 4,726,046 A * | 2/1988 | Nunan | A61N 5/1042 250/492.1 |
| 4,737,647 A | 4/1988 | Stieber et al. | |
| 4,827,491 A | 5/1989 | Barish | |
| 5,452,720 A | 9/1995 | Smith et al. | |
| 5,661,377 A | 8/1997 | Mishin et al. | |
| 5,684,854 A | 11/1997 | Hughes | |
| 5,729,584 A | 3/1998 | Moorman et al. | |
| 5,847,401 A * | 12/1998 | McKeown | G21K 5/04 250/396 ML |
| 5,859,893 A | 1/1999 | Moorman et al. | |
| 6,332,017 B1 | 12/2001 | Carroll et al. | |
| 6,333,966 B1 | 12/2001 | Schoen et al. | |
| 6,353,227 B1 | 3/2002 | Boxen | |
| 6,459,762 B1 | 10/2002 | Wong et al. | |
| 6,463,123 B1 | 10/2002 | Korenev | |
| 6,537,052 B1 | 3/2003 | Adler et al. | |
| 6,559,610 B2 | 5/2003 | Tanaka et al. | |
| 6,628,750 B1 | 9/2003 | Korenev | |
| 6,714,620 B2 | 3/2004 | Caflisch et al. | |
| 6,724,782 B2 | 4/2004 | Hartemann et al. | |
| 6,728,335 B1 | 4/2004 | Thomson et al. | |
| 6,768,265 B1 | 7/2004 | Ives et al. | |
| 6,794,656 B2 | 9/2004 | Francke et al. | |
| 6,847,168 B1 | 1/2005 | Ives et al. | |
| 6,937,693 B2 | 8/2005 | Svatos et al. | |
| 6,977,987 B2 | 12/2005 | Yamashita et al. | |
| 7,085,347 B2 | 8/2006 | Mihara et al. | |
| 7,164,748 B2 | 1/2007 | Francke | |
| 7,167,540 B2 * | 1/2007 | Muller | A61N 5/1084 378/65 |
| 7,180,243 B2 | 2/2007 | Secheresse et al. | |
| 7,190,764 B2 | 3/2007 | Mori et al. | |
| 7,206,379 B2 | 4/2007 | Lemaitre et al. | |
| 7,385,354 B2 | 6/2008 | Miyake | |
| 7,391,850 B2 | 6/2008 | Kaertne et al. | |
| 7,486,775 B2 * | 2/2009 | Forster | A61N 5/1081 250/492.3 |
| 7,601,966 B2 | 10/2009 | Ben-haim et al. | |
| 7,630,474 B2 | 12/2009 | Clayton et al. | |
| 7,741,624 B1 * | 6/2010 | Sahadevan | A61N 5/1081 250/341.7 |
| 7,816,870 B2 | 10/2010 | Yakovlev et al. | |
| 7,835,492 B1 | 11/2010 | Sahadevan et al. | |
| 7,838,838 B2 | 11/2010 | Rousso et al. | |
| 7,839,972 B2 | 11/2010 | Ruchala et al. | |
| 8,027,431 B2 | 9/2011 | Stahl et al. | |
| 8,039,819 B2 | 10/2011 | Faure et al. | |
| 8,139,714 B1 * | 3/2012 | Sahadevan | A61N 5/025 378/63 |
| 8,173,983 B1 * | 5/2012 | Sahadevan | A61N 5/1084 250/341.7 |
| 8,232,748 B2 | 7/2012 | Treas et al. | |
| 8,315,357 B2 | 11/2012 | Zhu et al. | |
| 8,350,226 B2 | 1/2013 | Zdasiuk et al. | |
| 8,405,044 B2 | 3/2013 | MacKinnon et al. | |
| 8,547,006 B1 | 10/2013 | Ives et al. | |
| 8,575,579 B2 | 11/2013 | Moskvin et al. | |
| 8,610,075 B2 | 12/2013 | Rousso et al. | |
| 8,618,521 B2 * | 12/2013 | Loo | A61N 5/1065 250/492.3 |
| 8,624,496 B2 | 1/2014 | Neubauer et al. | |
| 8,674,630 B1 | 3/2014 | Cornelius | |
| 8,787,529 B2 | 7/2014 | Graves et al. | |
| 9,018,603 B2 * | 4/2015 | Loo | A61N 5/1065 250/492.3 |
| 9,155,910 B1 * | 10/2015 | Sahadevan | A61N 5/1077 |
| 9,470,801 B2 | 10/2016 | Ziv et al. | |
| 9,764,161 B2 * | 9/2017 | Mazin | A61N 5/1065 |
| 9,804,104 B2 | 10/2017 | Libman et al. | |
| 9,931,522 B2 | 4/2018 | Bharadwaj et al. | |
| 9,962,562 B2 | 5/2018 | Fahrig et al. | |
| 2002/0090194 A1 * | 7/2002 | Tajima | H05H 15/00 385/147 |
| 2002/0191746 A1 | 12/2002 | Dinsmore et al. | |
| 2004/0044265 A1 * | 3/2004 | Muller | A61N 5/1084 600/1 |
| 2004/0079899 A1 | 4/2004 | Ma | |
| 2004/0082855 A1 | 4/2004 | Robar et al. | |
| 2004/0140432 A1 | 7/2004 | Maldonado et al. | |
| 2005/0167610 A1 * | 8/2005 | Tajima | G21K 1/003 250/423 P |
| 2006/0001855 A1 | 1/2006 | Lof et al. | |
| 2006/0056596 A1 * | 3/2006 | Mori | H05H 13/08 378/138 |
| 2006/0106301 A1 * | 5/2006 | Kats | A61N 5/10 600/415 |
| 2007/0051905 A1 | 3/2007 | Fujimaki et al. | |
| 2007/0076846 A1 * | 4/2007 | Ruchala | A61N 5/103 378/65 |
| 2007/0152610 A1 | 7/2007 | Yakovlev et al. | |
| 2007/0201613 A1 * | 8/2007 | Lu | A61N 5/1049 378/65 |
| 2007/0265230 A1 | 11/2007 | Rousso et al. | |
| 2008/0001090 A1 | 1/2008 | Ben-haim et al. | |
| 2008/0002811 A1 * | 1/2008 | Allison | A61N 5/1049 378/65 |
| 2008/0049897 A1 | 2/2008 | Molloy | |
| 2008/0081991 A1 * | 4/2008 | West | A61N 5/1031 600/425 |
| 2008/0144908 A1 * | 6/2008 | West | A61N 5/1031 382/131 |
| 2008/0298401 A1 | 12/2008 | Faure et al. | |
| 2009/0185656 A1 | 7/2009 | Heuscher | |
| 2009/0212231 A1 | 8/2009 | Hill et al. | |
| 2009/0225932 A1 | 9/2009 | Zhu et al. | |
| 2009/0252291 A1 | 10/2009 | Lu et al. | |
| 2009/0296885 A1 | 12/2009 | Boeh et al. | |
| 2010/0001200 A1 | 1/2010 | Ben-haim et al. | |
| 2010/0174180 A1 | 7/2010 | Rousso et al. | |
| 2010/0183206 A1 * | 7/2010 | Carlsen | A61B 6/032 382/128 |
| 2010/0207042 A1 | 8/2010 | Harada et al. | |
| 2010/0228116 A1 | 9/2010 | Lu et al. | |
| 2010/0246767 A1 * | 9/2010 | Tanabe | A61N 5/1049 378/65 |
| 2010/0260317 A1 | 10/2010 | Chang et al. | |
| 2011/0073778 A1 | 3/2011 | Natori et al. | |
| 2011/0093243 A1 | 4/2011 | Tawhai et al. | |
| 2011/0206187 A1 | 8/2011 | Lee et al. | |
| 2011/0254443 A1 | 10/2011 | Neubauer et al. | |

(56) References Cited

U.S. PATENT DOCUMENTS

| | | | |
|---|---|---|---|
| 2011/0266464 A1* | 11/2011 | Takai | A61N 5/1067 250/492.1 |
| 2012/0008735 A1* | 1/2012 | Maurer | A61B 6/025 378/5 |
| 2012/0022363 A1 | 1/2012 | Dempsey | |
| 2012/0085916 A1* | 4/2012 | Clayton | A61N 5/1001 250/395 |
| 2012/0262333 A1 | 10/2012 | Trummer et al. | |
| 2012/0305796 A1 | 12/2012 | Iseki et al. | |
| 2012/0326636 A1* | 12/2012 | Eaton | H05H 7/02 315/501 |
| 2013/0016814 A1 | 1/2013 | Treas et al. | |
| 2013/0035587 A1 | 2/2013 | Lagendijk et al. | |
| 2013/0172657 A1* | 7/2013 | Meier | A61N 5/1039 600/1 |
| 2013/0231516 A1* | 9/2013 | Loo | A61N 5/1043 600/1 |
| 2013/0287167 A1* | 10/2013 | Gum | G06T 7/0016 378/20 |
| 2014/0010351 A1 | 1/2014 | Rommel | |
| 2014/0037541 A1 | 2/2014 | Rousso et al. | |
| 2014/0119496 A1* | 5/2014 | Zhou | A61N 5/1069 378/4 |
| 2014/0135563 A1 | 5/2014 | Loo et al. | |
| 2014/0371581 A1* | 12/2014 | Mostafavi | A61B 6/5288 600/427 |
| 2015/0011817 A1* | 1/2015 | Feng | A61N 5/1077 600/1 |
| 2015/0016586 A1* | 1/2015 | Maurer, Jr. | A61B 6/4071 378/5 |
| 2015/0070029 A1 | 3/2015 | Libman et al. | |
| 2015/0087881 A1* | 3/2015 | Miyamoto | A61B 6/5211 600/1 |
| 2016/0014876 A1 | 1/2016 | Tantawi et al. | |
| 2016/0193481 A1* | 7/2016 | Tantawi | A61N 5/1039 600/1 |
| 2016/0193482 A1 | 7/2016 | Fahrig et al. | |
| 2016/0310764 A1* | 10/2016 | Bharadwaj | A61N 5/1064 |

FOREIGN PATENT DOCUMENTS

| | | |
|---|---|---|
| WO | 2005115544 | 12/2005 |
| WO | 2007140090 | 12/2007 |
| WO | 2011127946 | 10/2011 |
| WO | 2012025261 | 3/2012 |
| WO | 2013133936 | 9/2013 |
| WO | 2014055989 | 4/2014 |
| WO | 2015038832 | 3/2015 |
| WO | 2015102680 | 7/2015 |
| WO | 2015102681 | 7/2015 |

OTHER PUBLICATIONS

U.S. Appl. No. 15/896,407, "Non-Final Office Action", dated Mar. 1, 2019, 9 pages.
EP13757604.7, "Notice of Decision to Grant", dated Apr. 4, 2019, 2 pages.
EP13757604.7, "Summons to Attend Oral Proceedings", Apr. 16, 2019, 7 pages.
EP14876485.5, "Summons to Attend Oral Proceedings", Feb. 22, 2019, 4 pages.
Bazalova et al., "WE-C-BRB-05: Monte Carlo Simulations and Experimental Validation of Rapid Dose Delivery with Very High-Energy Electron Beams", Medical Physics, vol. 39, No. 6, Jun. 2012, p. 3944.
Brahme et al., "Electron and Photon Beams from a 50 MeV Racetrack Microtron", Acta Oncologica. vol. 19. No. 4, Jan. 1980, pp. 305-319.
Caryotakis, "Development of X-band Klystron Technology at SLAG", Proceedings of the 1997 Particle Accelerator Conference, vol. 3, May 1997, pp. 2894-2898.
Desrosiers et al., "150-250 MeV electron beams in radiation therapy", Physics in Medicine and Biology, vol. 45, No. 7, 2000, pp. 1781-1805.
Desrosiers et al., "An evaluation of very high energy electron beams (up to 250 MeV) in radiation therapy", Purdue University, Dec. 2004, 163 pages.
Dolgashev et al., "Geometric dependence of radio-frequency breakdown in normal conducting accelerating structures", Applied Physics Letters, vol. 97, No. 17, 2010.
Fuchs, "Laser-accelerated particles: Investigations towards applications in radiotherapy", Retrieved from internet: http://www.ub.uni-heidelberg.de/archiv/7452, 2007, 152 pages.
Fuchs et al., "Treatment planning for laser-accelerated very-high energy electrons", Physics in Medicine and Biology vol. 54, No. 11, 2009, pp. 3315-3328.
Furukawa et al., "Design study of a raster scanning system for moving target irradiation in heavy-ion radiotherapy", Medical Physics, vol. 34, No. 3, Mar. 2007, pp. 1085-1097.
Glinec et al., "Radiotherapy with laser-plasma accelerators: Monte Carlo simulation of dose deposited by an experimental quasimonoenergetic electron beam", Medical Physics, vol. 33, No. 1, Jan. 2006, pp. 155-162.
Howell et al., "Measurements of secondary neutron dose from 15 MV and 18 MV IMRT", Radiation Protection Dosimetry, vol. 115, issues 1-4, 2005, pp. 508-512.
Neilson et al., "Design of RF feed system and cavities for standing-wave accelerator structure", Nuclear Instruments and Methods in Physics Research A: Accelerators, Spectrometers, Detectors and Associated Equipment, vol. 657, issue 1, Nov. 2011, pp. 52-54.
Palowitz et al., "MCNPX 2.7.E Extension", Los Alamos National Laboratory report LA-UR-11-01502, draft of later publication Palowitz, Denise B. et al., MCNPX User's Manual, Version 2. 7.0, Mar. 2011.
Papaconstadopoulos et al., "WE-C-BRB-04: Fast and Accurate Hybrid Source Model for Modulated Electron Radiotherap", Medical Physics, vol. 39, No. 6, Jun. 2012, p. 3944.
International Search Report & Written Opinion dated Apr. 19, 2013 for PCT/US2013/025765, 20 pages.
International Search Report and Written Opinion dated Jul. 9, 2015 for PCT/US2014/055252, 8 pages.
International Search Report and Written Opinion dated Jul. 2, 2015 for PCT/US2014/055260, 7 pages.
International Search Report and Written Opinion dated Jan. 27, 2015 for PCT/US2014/055270, 16 pages.
Schneider et al., "Secondary neutron dose during proton therapy using spot scanning", International Journal of Radiation Oncology Biology Physics, vol. 53, issue 1, May 2002, pp. 244-251.
Tantawi et al., "rf distribution system for a set of standing-wave accelerator structures", Physical Review Special Topics—Accelerators and Beams, vol. 9, No. 11, Nov. 2006, pp. 112001-1-112001-6.
Ulmer, "On the Creation of High Energy Bremsstrahlung and Intensity by A Multitarget and Repeated Focusing of the u Scattered Electrons by a Small-Angle Backscatter at the Wall of a Cone and Magnetic Fields—A Possible Way to Improve Linear Accelerators in Radio..", Radiation Physics and Chemistry 81, 2012, pp. 387-402.
Walters et al., "DOSXYZnrc Users Manual", Ionizing Radiation Standards National Research Council of Canada, Retrieved from Internet: http://irs.inms.nrc.ca/software/beamnrc/documentation/pirs794, 2001, pp. 1-109.
Yeboah et al., "Optimization of intensity-modulated very high energy (50-250 MeV) electron therapy", Physics in Medicine and Biology, vol. 47, No. 8, 2002, pp. 1285-1301.
Yeboah et al., "Optimized treatment planning for prostate cancer comparing IMPT, VHEET and 15 MV IMXT", Physics in Medicine and Biology, vol. 47, No. 13, 2002, pp. 2247-2261.

* cited by examiner

RAPID IMAGING SYSTEMS AND METHODS FOR FACILITATING RAPID RADIATION THERAPIES

CROSS-REFERENCES TO RELATED APPLICATIONS

The present application is a Division of U.S. patent application Ser. No. 15/068,471 filed Mar. 11, 2016 (Allowed); which is a Continuation of PCT/US2014/055270 filed Sep. 11, 2014; which claims priority to U.S. Provisional Appln No. 61/876,679 filed Sep. 11, 2013; the entire contents of which are incorporated herein by reference in their entirety for all purposes.

This application is generally related to U.S. application Ser. No. 13/765,017, entitled "Pluridirectional Very High Electron Energy Radiation Therapy Systems and Processes," filed Feb. 12, 2013 (now U.S. Pat. No. 8,618,521); PCT Application No. PCT/US2014/055260 filed Sep. 11, 2014; and PCT Application No. PCT/US2014/055252 filed Sep. 11, 2014; the entire contents of which are incorporated herein by reference in their entirety for all purposes.

FIELD OF THE INVENTION

The invention generally relates to radiation therapies and more particularly to systems and methods for very rapid radiation therapies.

BACKGROUND OF THE INVENTION

Major technical advances in radiation therapy in the past two decades have provided effective sculpting of 3-D dose distributions and spatially accurate dose delivery by imaging verification. These technologies, including intensity modulated radiation therapy (IMRT), hadron therapy, and image guided radiation therapy (IGRT) have translated clinically to decreased normal tissue toxicity for the same tumor control, and more recently, focused dose intensification to achieve high local control without increased toxicity, as in stereotactic ablative radiotherapy (SABR) and stereotactic body radiotherapy (SBRT).

One key remaining barrier to precise, accurate, highly conformal radiation therapy is patient, target and organ motion from many sources including musculoskeletal, breathing, cardiac, organ filling, peristalsis, etc. that occurs during treatment delivery, currently 15-90 minutes per fraction for state-of-the-art high-dose radiotherapy. As such, significant effort has been devoted to developing "motion management" strategies, e.g., complex immobilization, marker implantation, respiratory gating, and dynamic tumor tracking.

BRIEF SUMMARY OF THE INVENTION

The present invention relates to methods and systems for facilitating radiation therapies, particularly extremely rapid radiation therapies that rapidly deliver a radiation treatment sufficiently fast enough to freeze physiologic motion.

In one aspect, the invention relates to a system for delivering radiation treatment to a targeted tissue in a patient that includes an array of accelerating structures, wherein each accelerating structure supplies beams to one or more beamlines that extend to a common target at the targeted tissue; and a programmable controller configured for controlling and directing power to select accelerating structures of the array so as to deliver an entire treatment dose to the targeted tissue from differing directions through the select accelerating structures. In some embodiments where the array defines nine or fewer beamlines, the accelerating structures are disposed on a rotatable gantry. The system may include one or more beam steering devices disposed within each of the accelerating structures of the array configured for receiving one or more particle beams and steering the one or more beams to the common target.

In some embodiments, the array is arranged in a radial array in which the accelerating structures are disposed radially at equidistant or non-equidistant intervals about a first longitudinal axis and a distal portion of each accelerating structure extend toward the common target at an acute angle, such as at an angle between 30 and 60 degrees. This configuration allows for an imaging device circumscribing the target tissue, such as a full CT ring and a beam dump positioned to absorb any remaining radiation passed through the target tissue.

In some embodiments, the system having an array of accelerators includes an RF power source that is common to all accelerating structures within the array, wherein the RF power source includes one or more RF power sources and a single RF power output provided through a phased array, wherein the phased array comprises a control unit configured such that the single RF power output alternates rapidly between the selected accelerating structures through source phasing controlled by the control unit so that an entire treatment dose can be delivered from multiple accelerating structures within the array in less than 10 seconds.

In one aspect, the invention relates to a method of treatment including steps of: obtaining a treatment image of an anatomical structure of the patient with an imaging system, the anatomical structure including the tissue targeted for treatment; determining a predicted shape and/or location of the anatomical structure at treatment based on the treatment image and one or more pre-treatment images obtained prior to obtaining the treatment image, wherein the predicted shape and/or location differs from that indicated by the treatment image; determining an actual treatment plan for the targeted tissue based on the treatment image and a treatment plan associated with the one or more pre-treatment images; and delivering a radiation treatment to the targeted tissue according to the actual treatment plan, wherein the entire dose of the radiation treatment is delivered in about 10 second or less. Obtaining the treatment image may include obtaining a full CT scan and determining an actual treatment plan from the CT scan, often within less than a minute, in some embodiments, in less than 10 seconds, so as to allow rapid radiation therapy. In some embodiments, the method includes performing registration with the full CT scan, wherein the full CT scan and registration is performed within about one second or less.

In another aspect, the invention relates to methods of imaging utilizing one of the same linear accelerators that is used for treatment. For example, such a method may include steps of: detuning a linear accelerator of a treatment system through which one or more electron beams are accelerated for delivering a radiation treatment; detuning the linear accelerator to generate an electron beam of lower energy than those of the one or more electron beams for treatment; and directing the lower-energy electrons to a high-Z target so as to produce a diagnostic energy spectrum suitable for imaging of the targeted tissue with the same linear accelerator as is used for acceleration of the one or more treatment beams. The method may further include determining a treatment plan based on a diagnostic image obtained using the lower-energy electron beam. After the image is obtained, the linear accelerator is tuned so as to provide a higher energy electron beam suitable for treatment according to the treatment plan in a short duration of time, such as within 10 seconds or less. The linear accelerator may be tuned concurrently with determining of the treatment plan so as to allow for planning and treatment, in less than one minute, often within 10 seconds or less.

In one aspect, the invention relates to a method of performing a radiation treatment that includes steps of: performing an initial simulation prior to treatment so as to produce a plurality of plans optimized for differing anticipated anatomical variations; at the time of treatment, acquire a diagnostic image covering the entire treatment volume of targeted tissue and surrounding tissue that may be traversed by one or more radiation treatment beams; performing re-segmentation of anatomic structures and recalculation or selection of treatment plan options from precalculated validated plans; verifying segmentation and selection of treatment plan options; and rapidly obtaining a treatment image and verifying selection a treatment plan from the treatment plan options within about one second or less, and then rapidly delivering a radiation treatment beam according to the determined and verified selected treatment plan, wherein an entire dose of the treatment is delivered within 10 seconds or less. In one aspect, re-segmentation is performed through a deformable image registration and may be automatic or semi-automatic so as to perform re-segmentation rapidly, such as within 10 seconds or less. Obtaining the diagnostic image may comprise obtaining a full CT scan. Verification and treatment plan selection may comprise automated or semi-automated rapid image comparison utilizing subtraction and/or registration. Such methods may further include steps of dynamic updating of the reconstruction during data acquisition until convergence is obtained on an optimal plan choice and the selected treatment plan such that the entire process is performed in less than 20 seconds and treatment is delivered in one second or less.

Delivery of radiation therapies in significantly reduced time-scale as compared to convention methods poses a number of difficulties, many of which are addressed by the methods and systems described herein. For example, aspects relating to targeted tissue motion, radiation beam generation and steering, power production and distribution, radiation source design, radiation beam control and shaping/intensity-modulation, treatment planning, imaging and dose verification present various challenges and, as used in conventional therapies, barriers to delivering radiation therapies to targeted tissues on a significantly reduced time scale. While the methods and systems described herein may be used to facilitate very rapid radiation therapies, particularly by addressing the above noted aspects of radiation delivery therapies, it is understood that these methods and systems are not limited to any particular radiation therapy delivery system or application described herein, and may be advantageous when used in various other radiation therapies and delivery systems, including conventional radiation therapies as well as non-medical applications.

A fundamentally different approach to managing motion is to deliver the treatment so rapidly that no significant physiologic motion occurs between verification imaging and completion of treatment. According to certain embodiments of the invention, an accelerator, more preferably a compact high-gradient, very high energy electron (VHEE) linear accelerator, which may be a standing wave linear accelerator, together with a delivery system capable of treating patients from multiple beam directions, potentially using all-electromagnetic or radiofrequency deflection steering is provided, that can deliver an entire dose or fraction of high-dose (e.g., 20-30 Gy) radiation therapy sufficiently fast to freeze physiologic motion, yet with a better degree of dose conformity or sculpting than conventional photon therapy. The term "sufficiently fast to freeze physiologic motion" in this document means preferably faster than one human breath hold, more preferably less than 10 seconds, even more preferably less than 5 seconds, even more preferably less than one heartbeat and most preferably less than a second. In addition to the unique physical advantages of extremely rapid radiation delivery, there may also be radiobiological advantages in terms of greater tumor control efficacy for the same physical radiation dose. Certain embodiments of the invention can also treat non-tumor targets, such as, by way of nonlimiting example, ablation or other treatment of: (1) nerves or facet joints for pain control; (2) foci in the brain for neuromodulation of neurologic conditions including pain, severe depression, and seizures; (3) portions of the lung with severe emphysema; and/or (4) abnormal conductive pathways in the heart to control refractory arrhythmias.

According to certain embodiments of the invention, there is provided a system for delivering very high electron energy beam to a target in a patient, comprising: an accelerator capable of generating a very high electron energy beam; a beam steering device capable of receiving the beam from the accelerator and steering the beam to the target from multiple directions; and a controller capable of controlling length of time that the beam irradiates the target, the length of time sufficiently fast to freeze physiologic motion, and to control the directions in which the beam steering device steers the beam to the target.

In certain embodiments, the controller is configured to receive information from an imaging device and use the information from the imaging device to control the directions in which the beam steering device steers the beam to the target. In some embodiments, the accelerator is a linear electron accelerator capable of generating a beam having energy of between 1 and 250 Mev, more preferably 50 and 250 MeV and most preferably between 75 and 100 MeV. In a rapid radiation treatment embodiment, the time period is preferably faster than one human breath hold, more preferably less than 10 seconds, even more preferably less than 5 seconds, even more preferably less than one heartbeat and most preferably less than a second.

According to some embodiments, providing the imaging device includes providing an imaging device that is capable of providing information to the controller to trigger when the system delivers the beam to the target. In some embodiments, providing the imaging device includes providing an imaging device wherein, using information from the imaging device, the system is capable of automatically delivering the beam to the target from multiple predetermined directions at multiple predetermined points in time.

BRIEF DESCRIPTION OF THE DRAWINGS

FIGS. 9A-1 through 9A-3 illustrate a beamline of a rapid radiation delivery system in accordance with certain embodiments.

DETAILED DESCRIPTION OF THE INVENTION

I. Rapid Radiation Treatment

A. Significance

Figure 1:
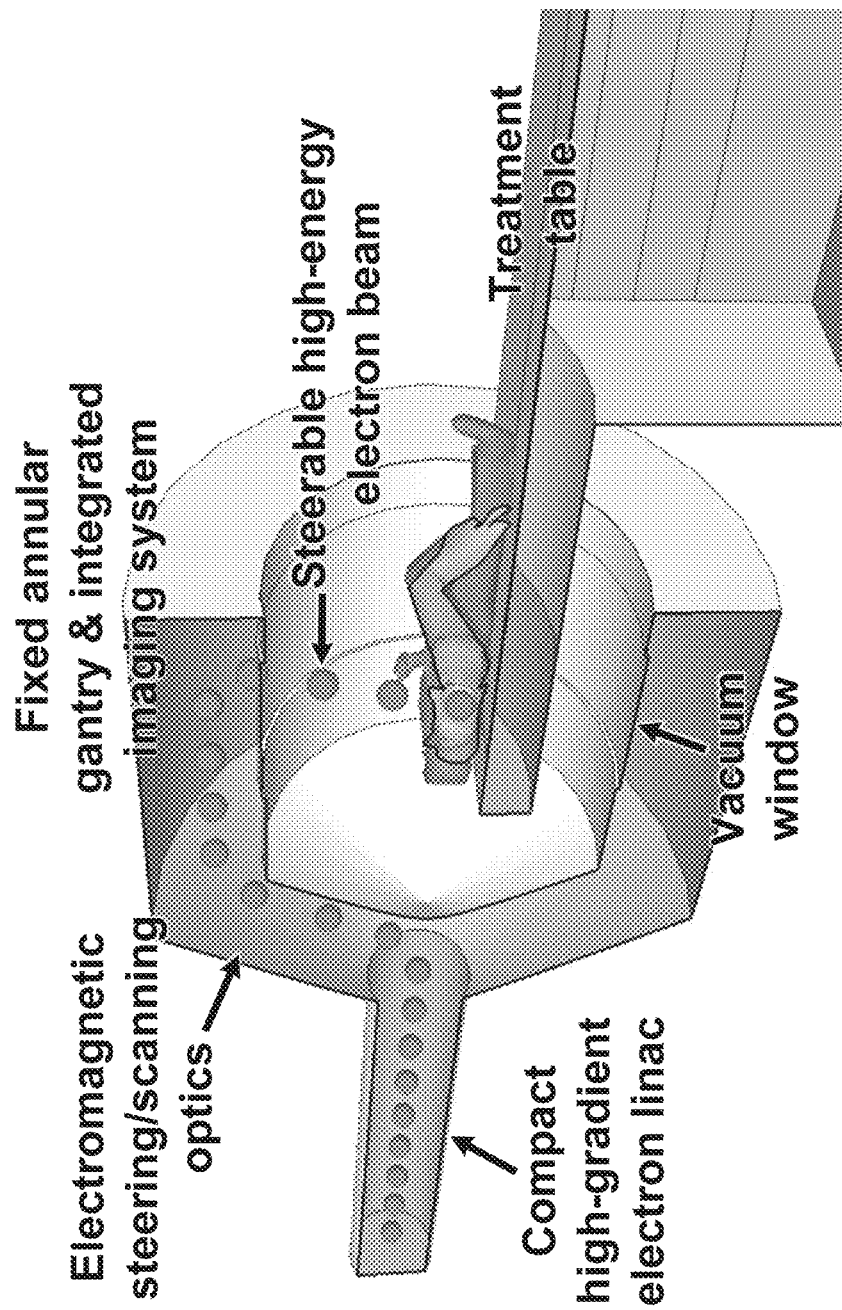
FIG. 1 is a schematic representation of a system in accordance with certain embodiments of the invention, showing beam access from a large number of axial directions by electromagnetic- or radiofrequency deflection steering.

In the U.S., cancer has surpassed heart disease as the leading cause of death in adults under age 85, and of the 1.5 million patients diagnosed with cancer each year, about two thirds will benefit from radiation therapy (RT) at some point in their treatment, with nearly three quarters of those receiving RT with curative intent. Worldwide, the global burden of cancer is increasing dramatically owing to the aging demographic, with an incidence of nearly 13 million per year and a projected 60% increase over the next 20 years, and the number of patients who could benefit from RT far exceeds its availability. Moreover, even when RT is administered with curative intent, tumor recurrence within the local radiation field is a major component of treatment failure for many common cancers. Thus, improvements in the efficacy of and access to RT have tremendous potential to save innumerable lives.

Although there have been major technological advances in radiation therapy in recent years, a fundamental remaining barrier to precise, accurate, highly conformal radiation therapy is patient, target, and organ motion from many sources including musculoskeletal, breathing, cardiac, organ filling, peristalsis, etc. that occurs during treatment delivery. Conventional radiation delivery times are long relative to the time scale for physiologic motion, and in fact, more sophisticated techniques tend to prolong the delivery time, currently 15-90 minutes per fraction for state-of-the-art high-dose radiotherapy. The very fastest available photon technique (arc delivery with flattening filter free mode) requires a minimum of 2-5 min to deliver 25 Gy. Significant motion can occur during these times.

Even for organs unaffected by respiratory motion, e.g., the prostate, the magnitude of intrafraction motion increases significantly with treatment duration, with 10% and 30% of treatments having prostate displacements of >5 mm and >3 mm, respectively, by only 10 minutes elapsed time. As such, considerable effort has been devoted to developing "motion management" strategies in order to suppress, control, or compensate for motion. These include complex immobilization, fiducial marker implantation, respiratory gating, and dynamic tumor tracking, and in all cases still require expansion of the target volume to avoid missing or undertreating the tumor owing to residual motion, at the cost of increased normal tissue irradiation.

Several factors contribute to long delivery times in existing photon therapy systems. First, production of x-rays by Bremsstrahlung is inefficient, with less than 1% of the energy of the original electron beam being converted to useful radiation. Second, collimation, and particularly intensity modulation by collimation, is similarly inefficient as the large majority of the beam energy is blocked by collimation. Third, using multiple beam angles or arcs to achieve conformal dose distributions requires mechanical gantry motion, which is slow. Treatment using protons or other heavier ions has dosimetric advantages over photon therapy, and these particles can be electromagnetically scanned very rapidly across a given treatment field. However changing beam directions still requires mechanical rotation of the massive gantry, which is much larger and slower than for photon systems. The cost and size of these systems also greatly limits their accessibility.

Very high-energy electrons (VHEE) in the energy range of 50-250 MeV have shown favorable dose deposition properties intermediate between megavoltage (MV) photons and high-energy protons. Without the need for inefficient Bremsstrahlung conversion or physical collimation, and with a smaller steering radius than heavier charged particles, treatment can be multiple orders of magnitude faster than any existing technology in a form factor comparable to conventional medical linacs. According to certain embodiments of the invention, a compact high-gradient VHEE accelerator and delivery system is provided that is capable of treating patients from multiple beam directions with great speed, using electro-magnetic, radiofrequency deflection or other beam steering devices. Such embodiments may deliver an entire dose or fraction of high-dose radiation therapy sufficiently fast to freeze physiologic motion, yet with a better degree of dose conformity or sculpting, and decreased integral dose and consequently decreased risk of late toxicities and secondary malignancies, than the best MV photon therapy. Suitable energy ranges in accordance with certain embodiments of the invention are 1-250 MeV, more preferably 50-250 MeV, and most preferably 75-100 MeV. Again, as described in the Summary section above, the term "sufficiently fast to freeze physiologic motion" in this document means preferably faster than one human breath hold, more preferably less than 10 seconds, even more preferably less than 5 seconds, even more preferably less than one heartbeat and most preferably less than a second.

According to some embodiments, a major technological advance is extremely rapid or near instantaneous delivery of high dose radiotherapy that can eliminate the impact of target motion during RT, affording improved accuracy and dose conformity and potentially radiobiological effectiveness that will lead to improved clinical outcomes. Rapid imaging and treatment can also lead to greater clinical efficiency and patient throughput. For standard treatments, the room occupancy time can be reduced to less than 5 minutes. There can also be a great practical advantage for special populations like pediatric patients who normally require general anesthesia for adequate immobilization during long treatments, and who can instead be treated with only moderate sedation for such rapid treatments. Such advantages can be achieved, according to some embodiments, in a compact physical form factor and low cost comparable to conventional photon therapy systems, and much lower than hadron therapy systems. One embodiment is shown in FIG. 1, which shows a system wherein beam access from a large number of axial directions is achieved by electromagnetic steering without moving parts or with a minimum of moving parts, for extremely fast highly conformal radiotherapy. The system shown in FIG. 1 includes a compact linear accelerator, a beam steering device, and a controller for controlling the very high electron energy beam that is delivered to the patient. The embodiment can also include an integrated imaging device that obtains images of portions of the patient including the tumor or other site to be treated. The imaging device can also provide information to allow for control of the beam steering device in order to control directions from which the beam is delivered, and timing of the beam, among other variables.

Furthermore, the prolonged treatment times of conventional highly conformal RT are sufficiently long for repair of sublethal chromosomal damage to occur during treatment, potentially reducing the tumoricidal effect of the radiation dose. Thus in addition to the unique physical advantages of extremely rapid radiation delivery, there may also be dose advantages. It is hypothesized that the treatment times sufficiently fast to freeze physiologic motion that are made possible by certain embodiments of the invention may be more biologically effective, producing enhanced tumor cell killing for the same physical dose. Differences between certain embodiments of the invention and conventional photon therapy that impact biological effectiveness include a much faster delivery time and differences in the radiation quality.

Dose rate effects are well described in the radiobiology literature, in which prolongation of delivery times results in decreased cell killing. The main mechanism known to be responsible for this effect is repair of potentially lethal DNA double strand breaks (DSB) during the interval over which a given dose of radiation is delivered. Several in vitro studies have demonstrated significantly decreased cell killing when delivery is protracted from a few minutes to tens of minutes. However, there is a lack of consensus in the literature regarding the kinetics of sublethal damage (SLD) repair, with some studies suggesting that components of SLD repair may have repair half-times of as little as a few minutes. If so, shortening the delivery times even from a few minutes to a time period sufficiently fast to freeze physiologic motion has the potential to increase tumor cell killing.

B. Beam Steering

Some embodiments of the invention take advantage of the fact that electrons are relatively easier to manipulate using electric and magnetic fields. Charged particles such as electrons and protons can be produced as spatially coherent beams that can be steered electromagnetically or with radiofrequency deflection with high rapidity. Thus, direct treatment with scanned charged particle beams can eliminate the inefficiencies of Bremsstrahlung photon multiple beams from different directions toward the target in the patient. All conventional radiation therapy systems accomplish multidirectional treatment by mechanically rotating a gantry, or an entire compact linac, or even cyclotron, directing radiation to the target from one direction at a time.

As a preliminary matter, at the end of the accelerator structure the beam must be deflected and then transported to the exit port and toward a target in or on the patient, such as a tumor in the patient. At the exit port the beam must be steered again to change the exit angle and/or beam size to adapt to the treatment plan. Electro-magnetic and/or RF deflector steering systems will manipulate the electron beam.

A variety of gantry designs are potentially available, from simple to complex, ranging from multiple discrete beam ports arranged around the patient to a continuous annular gantry to allow arbitrary incident axial beam angles. The design depends on a number of factors, including scanning strategies such as thin pencil beam raster scanning vs. volume filling with non-isocentric variable-size shots, or use of transverse modulation of the electron beam profile.

According to one embodiment, the steering system of the electron beam starts at the end of the accelerator structure with a two-dimensional deflector, which guides the beam into one of multiple channels. Once the beam enters a specific channel it is guided all the way to the exit of the channel, which is perpendicular to the axis of the patient. The guidance through the channels is achieved using low aberration electron optics. At the exit of each channel another small 2-D deflector can be added to scan the beam over a target. The number of channels can then be about 10-50. For a given channel width, a larger initial deflection would increase the number of channel entry ports that fit into the circumference swept by the beam. Thus if the field strength were increased, the number of channels could be increased to 100 or more.

Because a linear accelerator will typically consume 50 to 100 MW of peak power to achieve 100 MeV of acceleration, over a length of 2 to 1 m respectively, potential RF deflectors can be considered. These have the advantage of being ultra-fast and permit capitalization on the RF infrastructure that is used for the main accelerator structure. In any event, the delivery system is preferably optimized to achieve high-dose treatment times sufficiently fast to freeze physiologic motion.

Beam steering systems according to certain embodiments of the invention adopt a design that uses a smaller number of discrete beam channels, for example 3-10, that are mechanically rotated with the gantry around the patient. The initial deflector at the exit of the accelerator rapidly steers beams into the channels as they rotate. Although the ideal is to eliminate the need for any mechanical moving parts, some advantages of this design include: arbitrary rotational angular resolution despite a fixed number of beam channels;

reduced complexity and possibly cost given the smaller number of beam channels needed to achieve equivalent angular coverage; and the larger space between beam channels which makes it more straightforward to incorporate an x-ray source and detecting array for imaging, which when rotated provides integrated computed tomography imaging. The rate of mechanical rotation preferably provides full angular coverage sufficiently fast to freeze physiologic motion. The greater the number of beam channels, the less rotational speed required to meet this condition as a general matter.

One innovation of certain embodiments of the invention is to eliminate mechanical gantry rotation, thus a beam steering system with no mechanical moving parts. One such embodiment is illustrated in FIG. 1, in which there is a gantry through which a charged particle beam is electromagnetically steered or steered using radiofrequency deflection to the target from any axial direction and a limited range of non-coplanar directions in addition. Another implementation is to have multiple accelerating structures arranged in an array around the patient, one for each of a set of beam ports arranged radially around the patient.

Such novel treatment system geometries and steering systems can greatly enhance the treatment delivery speed of radiation therapy using any type of charged particle. Combining it with high-energy electrons in the 1-250 MeV range, more preferably the 50-250 MeV range, most preferably the 75-100 MeV range, has the following additional advantages: (1) Conformal dose distributions to both superficial and deep targets in patients superior to what can be achieved with conventional high-energy photon therapy; (2) Compactness of the source and power supply, which by using high-gradient accelerator designs such as those based wholly or partially on accelerators developed or in development at the SLAC National Accelerator Laboratory (SLAC) as described in Section C.iii below can accelerate electrons up to these energies in less than 2 meters; (3) Compactness of the gantry/beam ports compared to protons or ions because of the smaller electro-magnetic fields needed for electrons. This results in a system of comparable cost and physical size to existing conventional photon radiotherapy treatment systems, yet with better dose distributions and far faster dose delivery.

If treatment with photon beams is still desired, an alternative embodiment is to incorporate in this geometry an array of high density targets and collimator grid in place of a single target/multi-leaf collimator combination, one per beam port in the case of discrete beam ports, or mounted on a rapidly rotating closed ring and targeted by the scanned electron beam in the case of an annular beam port, in order to produce rapidly scanned, multidirectional photon beams. While this approach may be subject to the inefficiency of Bremsstrahlung conversion, the speed limitations of conventional mechanical gantry and multi-leaf collimator motions may be essentially eliminated. The main potential advantage of this implementation is that existing commercial electron linacs in a lower energy range could be used as the source.

In addition to extremely rapid dose delivery, certain embodiments of the invention naturally facilitate rapid image-guidance to ensure accuracy. By adjusting the energy of the scanned electron beam and directing it to an annular target or a fixed array of targets, with an appropriately arranged detector array, extremely fast x-ray computed tomography (CT) or digital tomosynthesis images can be obtained and compared to pre-treatment planning images immediately before delivery of the dose. Alternative embodiments can include integration of more conventional x-ray imaging or other imaging modalities, positron emission tomography and other options described further below.

C. Monte Carlo Simulation Design Considerations

One approach in designing certain embodiments of the invention is to proceed using some or all of the following: (1) Monte Carlo simulations to determine optimal operating parameters; (2) experimental measurements of VHEE beams to validate and calibrate the Monte Carlo codes; (3) implementation factors for practical, cost-efficient and compact designs for the systems; and (4) experimental characterization of key radiobiological aspects and effects.

1. Monte Carlo (MC) Simulation

MC simulations of VHEE of various energies have been performed on a sample case to estimate the range of electron energies needed to produce a plan comparable to optimized photon therapy. Dose distributions were calculated for a simulated lung tumor calculated on the CT data set of an anthropomorphic phantom.

Specifically, an optimized 6 MV photon beam Volumetric Modulated Arc Therapy Stereotactic Ablative Body Radiotherapy (VMAT SABR) plan calculated in the Eclipse treatment planning system, and simplistic conformal electron arc plans with 360 beams using a commonly available 20 MeV energy and a very high 100 MeV energy calculated with the EGSnrc MC code were compared. (See Walters B, Kawrakow I, and Rogers DWO, DOSXYZnrc, Users Manual, 2011, Ionizing Radiation Standards National Research Council of Canada. p. 1-109., available online at (http://irs.inms.nrc.ca/software/beamnrc/documentatio n/pirs794/), incorporated herein by this reference).

Figure 2:
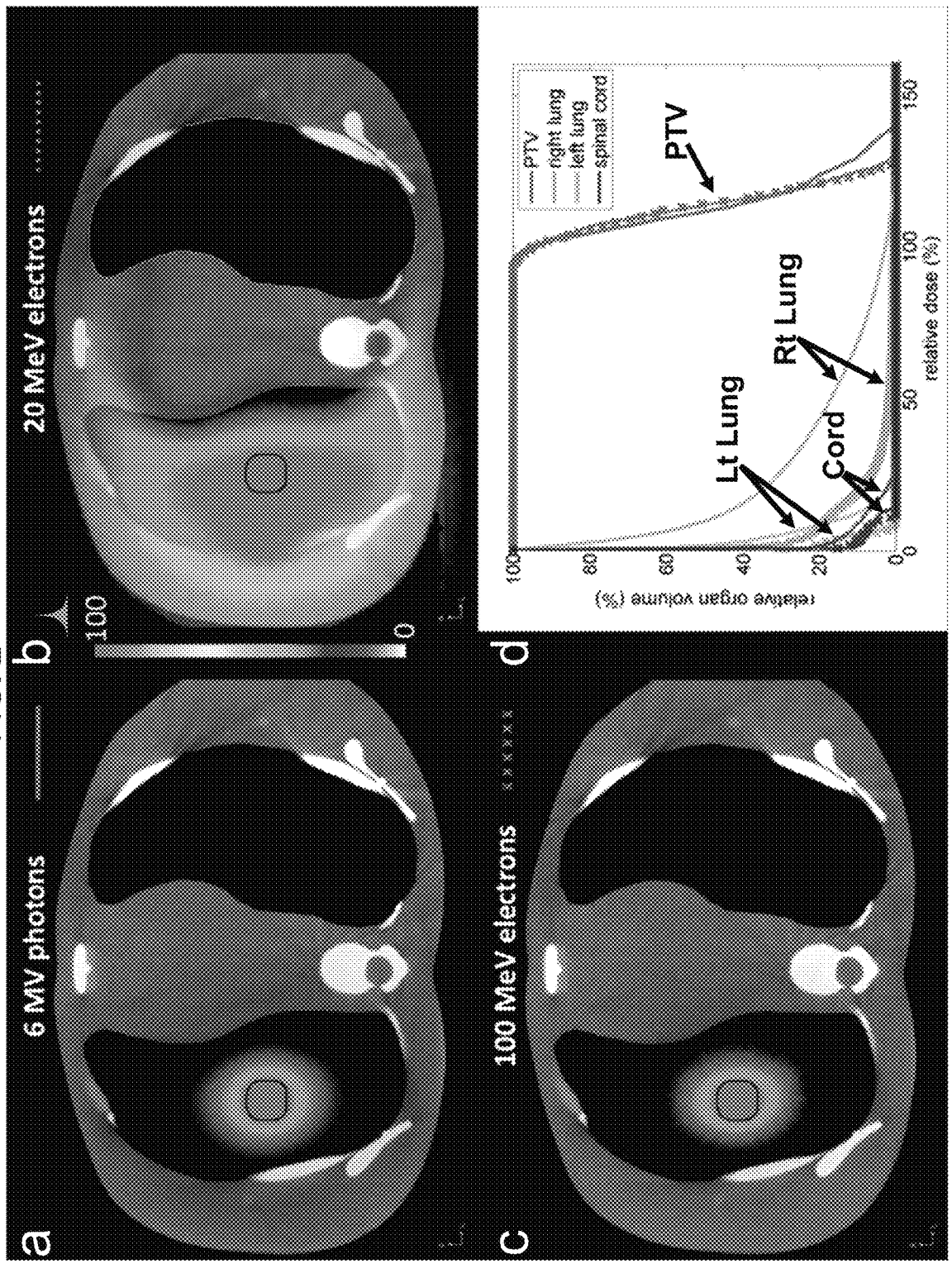
FIGS. 2a-2f show comparative simulation results of SABR for an early stage lung tumor using 6 MV photons, 20 MeV electrons, and 100 MeV electrons.
Figure 2:
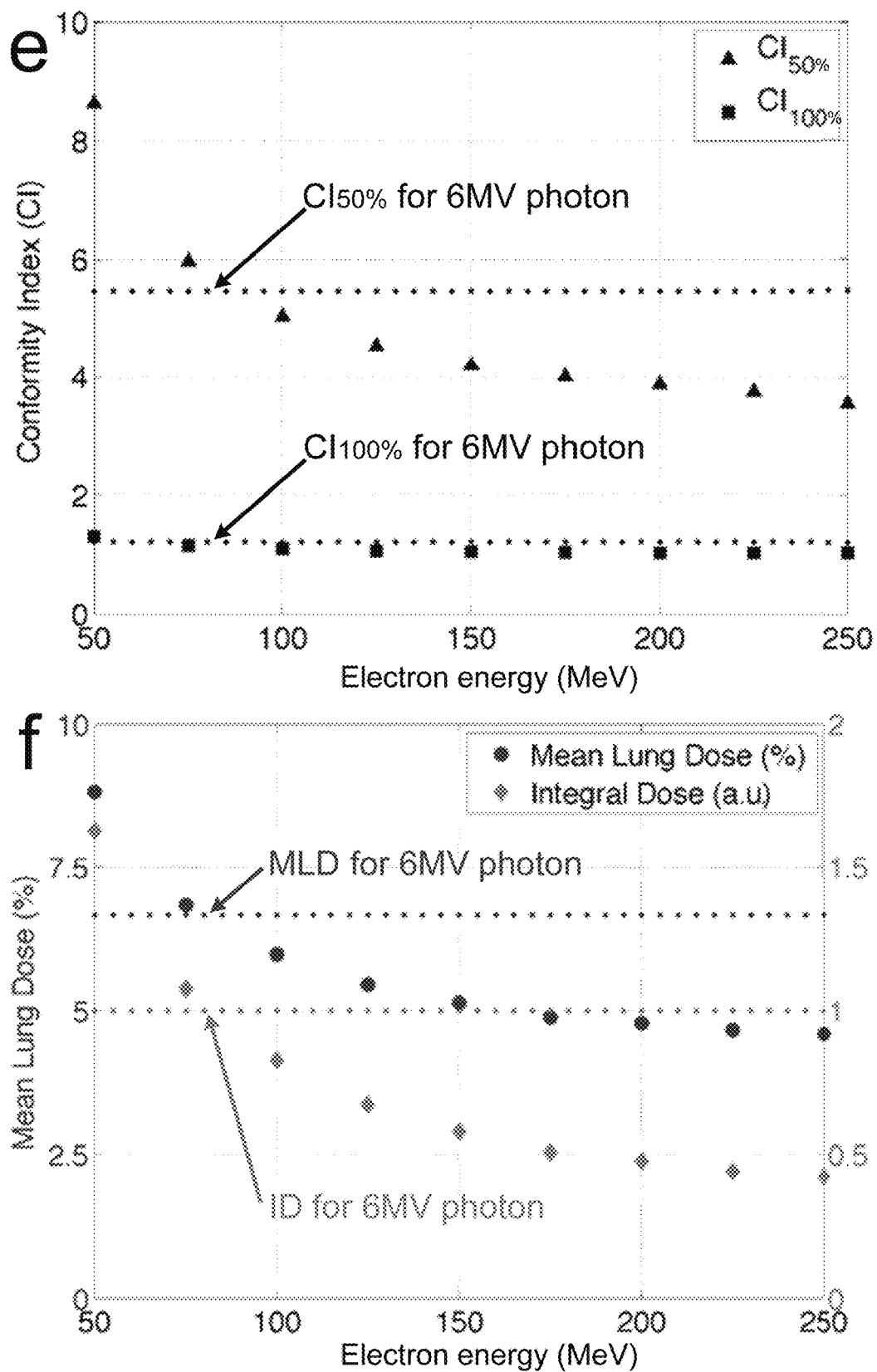

FIG. 2 shows axial images of simulation of SABR for an early stage lung tumor: dose distribution in an anthropomorphic phantom for a state-of-the-art 6 MV photon VMAT plan (FIG. 2a), a conformal electron arc plan using currently available 20 MeV electron beam (FIG. 2b), and a conformal electron arc plan using a 100 MeV electron beam as might be delivered by an embodiment of the invention (FIG. 2c). A graphical representation shows dose volume histogram ("DVH") of the planning target volume ("PTV") (delineated in black in the axial images) and critical organs: DVHs for 6 MV photons are shown in solid, 20 MeV electrons in dotted, and 100 MeV electrons in crossed lines (FIG. 2d). The plans were normalized to produce the same volumetric coverage of the PTV by the prescription dose. While conventional 20 MeV electrons results in poor conformity, the 100 MeV electron plan, even without optimization, is slightly more conformal than the 6 MV photon VMAT plan. Simulating conformal electron arcs across an energy range of 50-250 MeV (FIGS. 2e, 2f) demonstrates that both the high (100%) and intermediate (50%) dose conformity indices (CI 100% and CI 50%) as well as the mean lung dose and total body integral dose are superior for electron energies of ~80 MeV and higher for this selected clinical scenario. With inverse optimization, superior plans with even lower electron energies should be possible.

As shown in FIG. 2, the axial views of the dose distributions demonstrate that when all the plans are normalized to produce the same volumetric coverage of the target, the dose conformity of the 20 MeV beam is poor whereas the 100 MeV electron beam, even without inverse optimization, generates a dose distribution equivalent to the state-of-the-art 6 MV photon beam VMAT plan. In fact, the DVH's of the target and critical structures for the three beams demonstrate slightly better sparing of critical structures with the 100 MeV electron plan compared to the 6 MV photon plan. As shown in FIGS. 2e and 2f, at electron energies above ~80

MeV, simple conformal electron arc plans (normalized to produce the same volumetric coverage of the target) are superior to the optimized 6 MV photon VMAT plan in terms of conformity, with conformity index defined as the ratio of the given percent isodose volume to the PTV, and the normal organ doses (mean lung dose) and total body integral dose (expressed in arbitrary units normalized to the photon plan). In preliminary simulations of this selected clinical scenario, the inventors have found electron energies of 75-100 MeV to produce plans of comparably high to superior quality compared to the best photon plans, and anticipate that plan optimization will produce superior plans with even lower electron energies. For example, the inventors have used Monte Carlo simulations to demonstrate that an 8 cc lung tumor could be treated with 100 MeV electrons to a dose of 10 Gy in 1.3 seconds.

Further optimization of the electron plan can help to define the minimum electron beam energy with a comparable dose distribution to the best photon VMAT plan. In preliminary simulations of this selected clinical scenario, the inventors have found electron energies of 75-100 MeV to produce plans of comparably high quality to the best photon plans, and anticipate superior plans with plan optimization.

2. Experimental Measurement of VHEE Beams a. Monte Carlo Simulations

Figure 3:
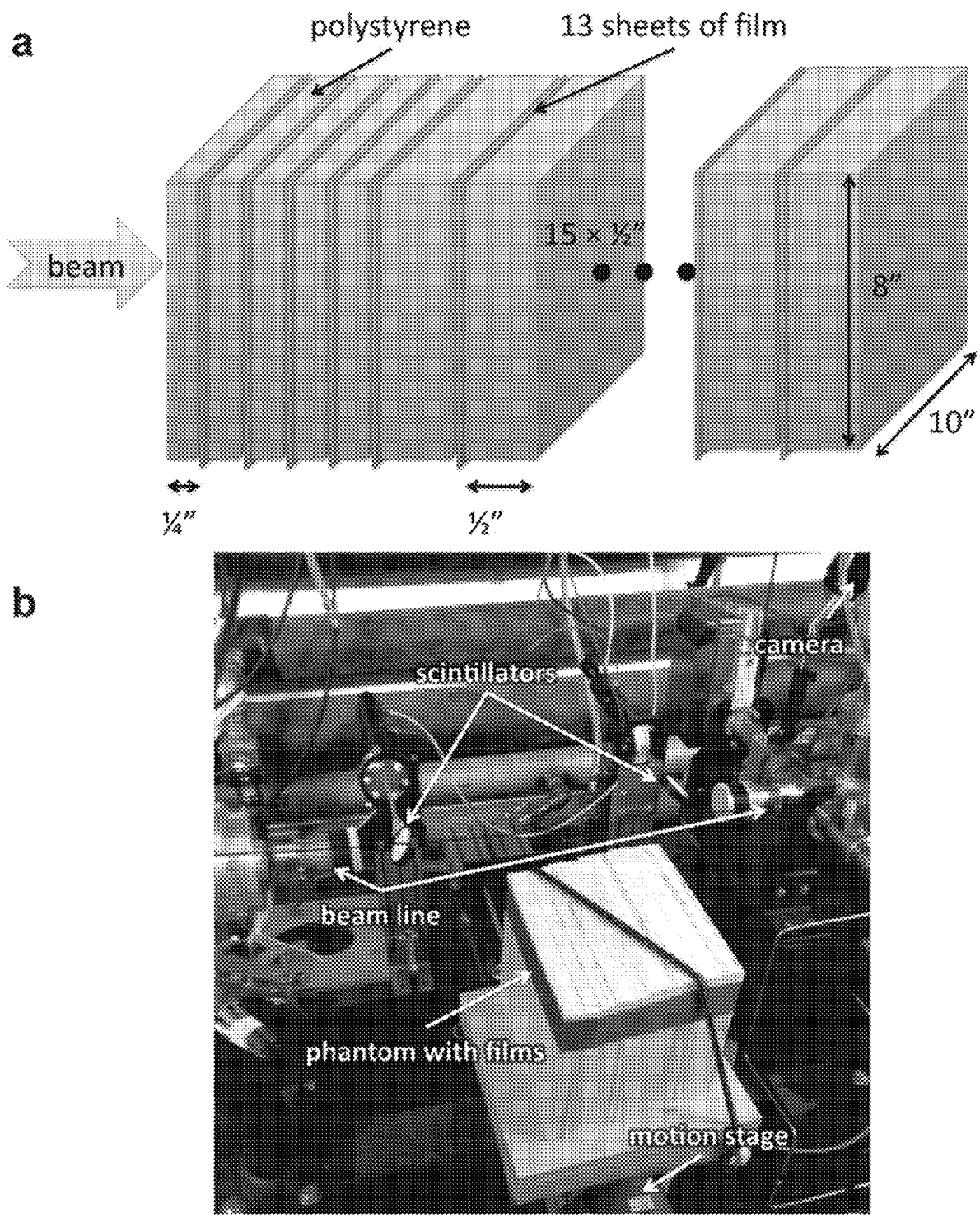
FIG. 3 is a schematic (a) and photograph (b) of the experimental setup for film measurements (c) of very high energy electron beams at the Next Linear Collider Test Accelerator (NLCTA) beam line at the SLAC National Accelerator Laboratory (SLAC), together with Monte Carlo simulations (solid lines) and film measurements (markers) of percentage depth dose curves (d) and beam profiles taken at 6 mm depth (e) for 50 MeV and 70 MeV beams, respectively.
Figure 3:
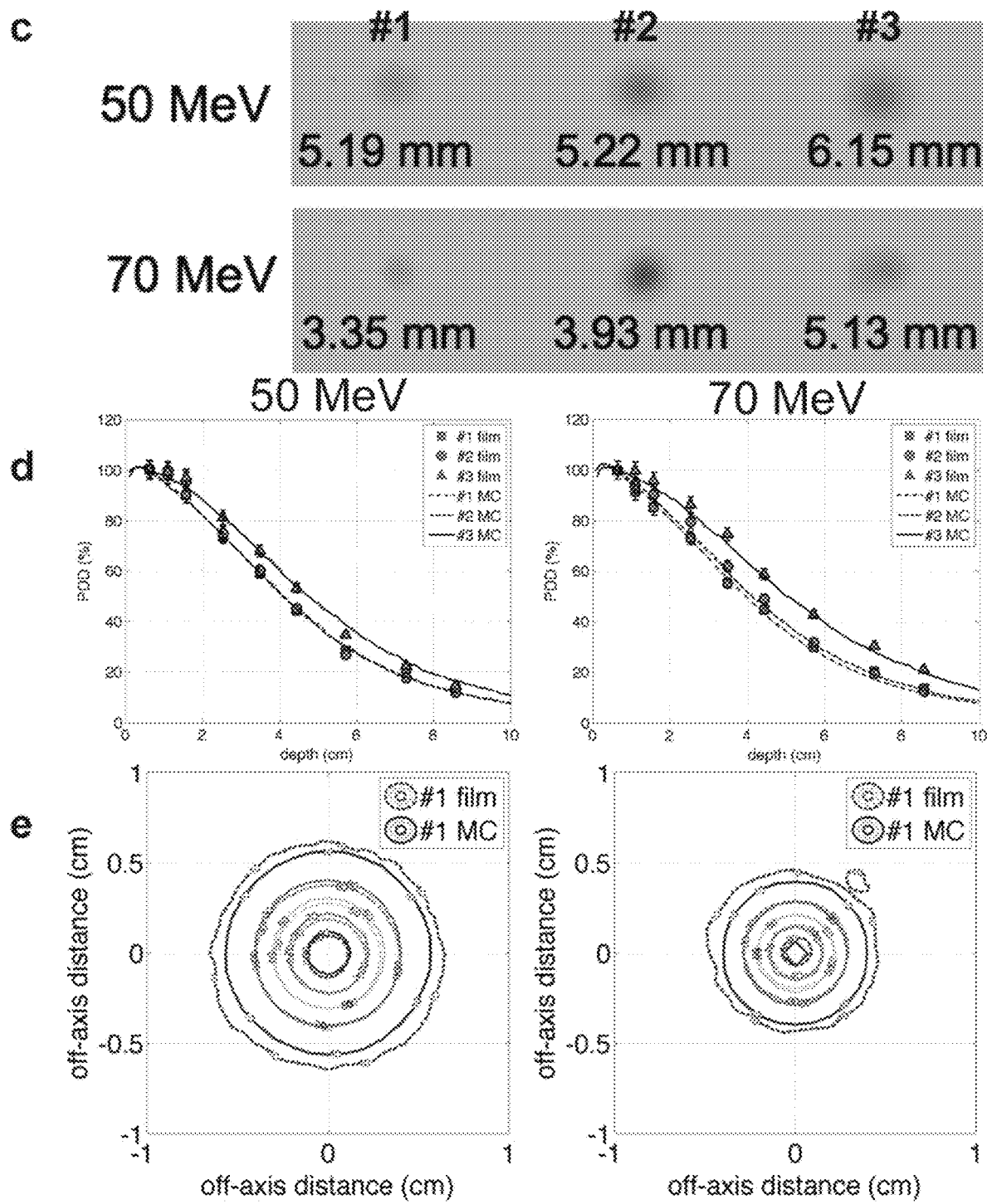

To demonstrate the accuracy of Monte Carlo calculations with VHEE beams, the inventors experimentally measured the dose distribution and depth dose profiles at the NLCTA facility at SLAC. Of note, the NLCTA employs compact high-gradient linear accelerator structures which can produce beams that are relevant to those potentially suitable for certain embodiments of the invention. The inventors assembled a dosimetry phantom by sandwiching GAFCHROMIC EBT2 films (International Specialty Products, Wayne, N.J.) between slabs of tissue equivalent polystyrene as shown in FIG. 3. FIG. 3a is a schematic and FIG. 3b is a photograph of the experimental setup for film measurements (FIG. 3c) of very high-energy electron beams at the NLCTA beam line at SLAC. Monte Carlo simulations and film measurements of percentage depth dose curves (FIG. 3d) and 2-D dose distributions taken at 6 mm depth (FIG. 3e) for 50 MeV and 70 MeV beams demonstrate a high degree of agreement between calculation and measurement.

By way of procedure and in greater detail, the phantom as shown in FIG. 3a was irradiated with 50 MeV and 70 MeV beams. Three beam sizes ranging from 3.35 to 6.15 mm were tested for each energy level. The energy was measured by a spectrometer upstream from the location of the experiment and the beam size was measured by two scintillating screens using two cameras just before and after the phantom with the phantom removed from the beam line (FIG. 3b). The films were calibrated with a clinical electron beam at 12 MeV. MC simulations have demonstrated no energy dependence of the film response at electron energies above 1 MeV. The number of particles required to irradiate the films to dose levels between 1-5 Gy to match the dynamic range of the film was determined for each beam size using MC simulations and used in the experiment. The charge was set to 30 pC/pulse corresponding to $1.9 \times 10^8$ electrons and the pulse rate was reduced to 1 Hz for easier control of the exposure. The number of pulses varied from 2 to 40 pulses depending on the beam size. The experimental and calibration films were read out in a flatbed scanner (Epson Perfection V500, Long Beach, Calif.) with 0.1 mm pixels 24 hours after irradiation (FIG. 3c) and central axis percentage depth dose (PDD) curves and 2-dimensional dose distributions at various depths were plotted. The experimental setup was simulated in MCNPX 5.0 MC code. (See Palowitz DB, MCNPX User's Manual, Version 2.7.0, 2011. available online at (http://mcnpx.lanl.gov/documents.html), incorporated herein by reference).

The simulations are compared to measurements in FIGS. 3d-e. Good agreement was observed for both the PDD curves and beam profiles for 50 and 70 MeV. These preliminary results indicate that dose from VHEE beams can be measured with GAFCHROMIC films and that VHEE beams can be accurately simulated with the GEANT4 code.

In the arrangement shown in FIG. 3b, a 50-μm vacuum window made of stainless steel was used to interface the accelerator line with open air, in which the dose phantom (FIG. 2a) was placed. The stainless window was found to cause significant angular beam spreading, so that the simulations were also performed with a beryllium window which imparted less beam spreading. While a vacuum window is necessary to separate the vacuum of the accelerator beam line from the open air and the patient, significant angular spread will adversely affect beam performance and clinical accuracy. The angular spread from a thinner beryllium window was still present but it was much smaller than steel, due to beryllium's low atomic number.

b. Cross Validation of Monte Carlo Codes

Figure 4:
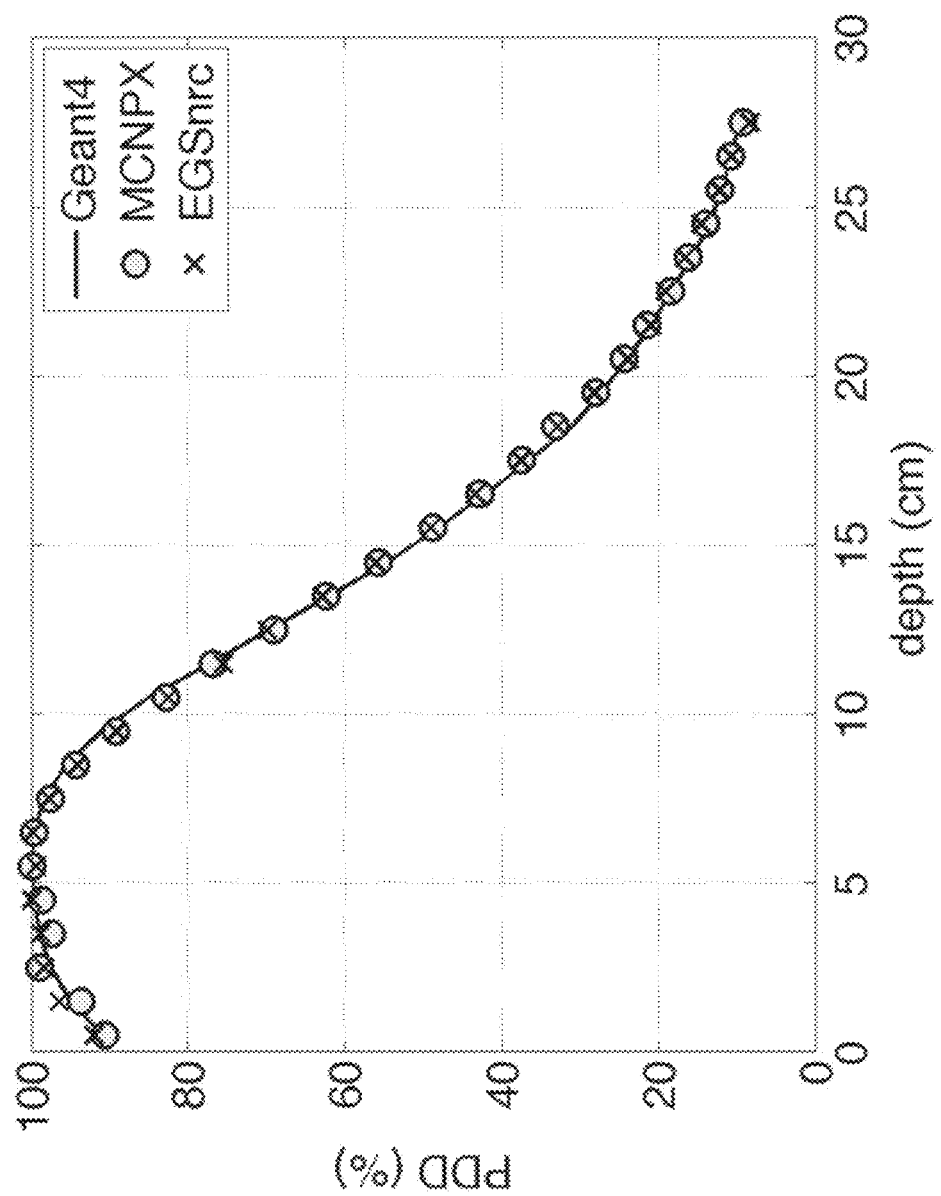
FIG. 4 shows graphic representations of percentage depth doses for a 2×2 cm 100 MeV electron beam in a water phantom, simulated using three independent Monte Carlo codes.
Figure 7:
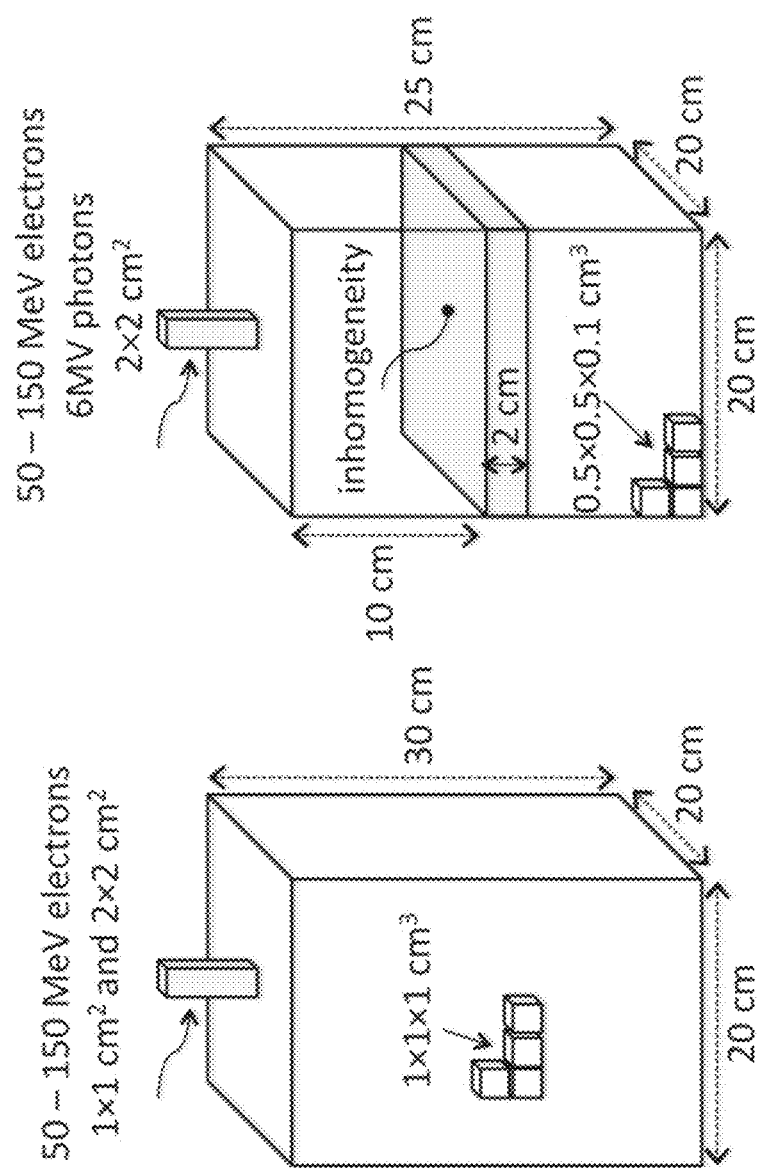
FIG. 7 shows water phantoms used in Monte Carlo simulations conducted in accordance with certain embodiments.

The inventors performed Monte Carlo simulations using three independent codes for identical geometries to determine the consistency of calculated doses. The dose deposition of a number of rectangular electron beams incident on a 20×20×30 cm water phantom (as shown in FIG. 7a) was simulated in the GEANT4, MCNPX, and EGSnrc MC codes. The simulated electron beam energies were 50, 75, 100, and 150 MeV with beam sizes of 1×1 cm and 2×2 cm. The central-axis PDDs were plotted and compared for all three MC codes. Excellent agreement was found between the codes for all of these comparisons, as shown in FIG. 4, which shows PDD for a 2×2 cm 100 MeV electron beam, simulated using the three Monte Carlo codes.

c. VHEE Tissue Interactions

Figure 5:
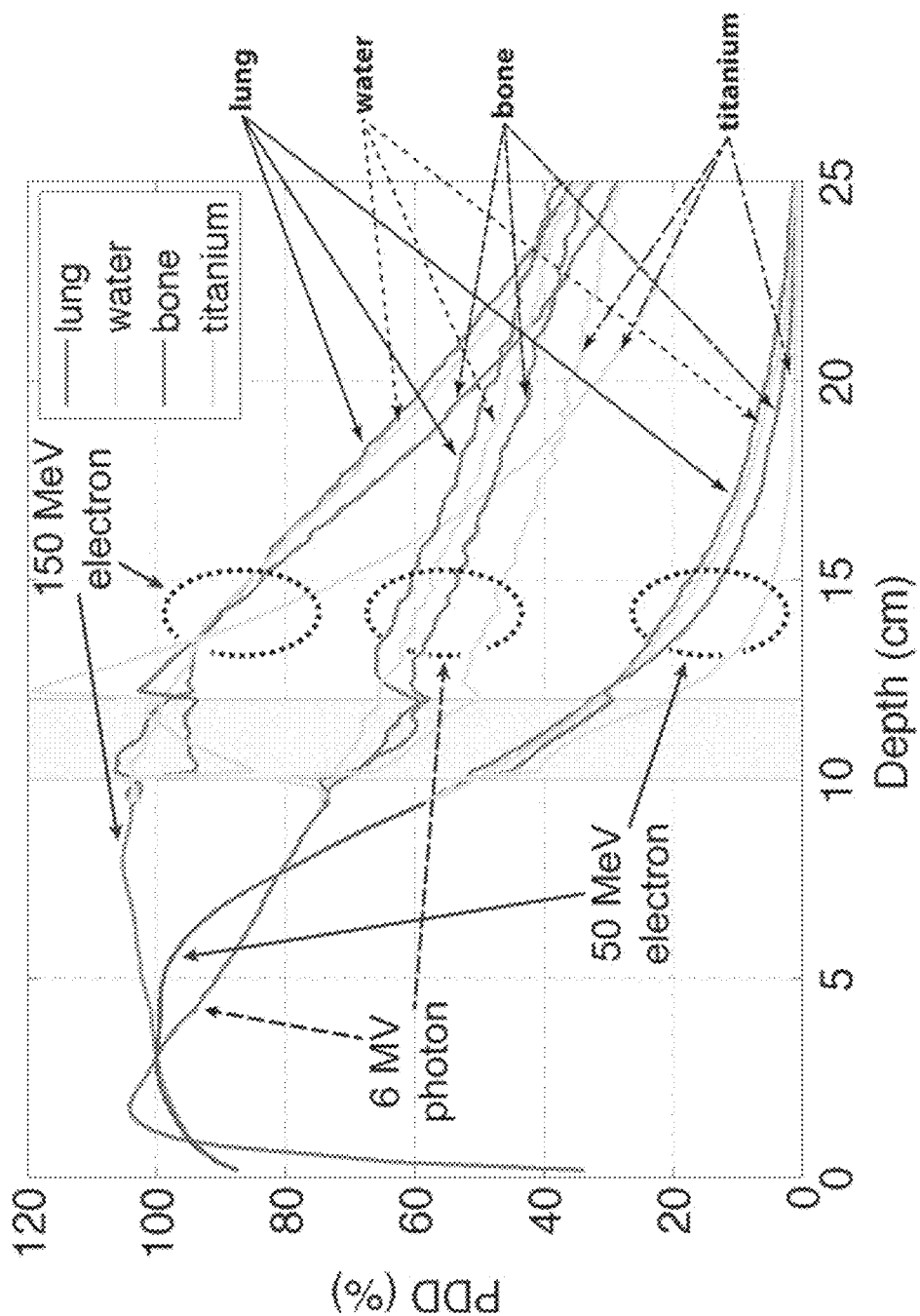
FIG. 5 shows graphic representations of percentage depth doses for 2×2 cm 50 and 150 MeV electron beams compared to 6 MV photons in a water phantom, with 2 cm thick heterogeneous tissue at 10 cm depth.

Monte Carlo simulations were performed to evaluate the impact of various tissue heterogeneities on VHEE beams relative to MV photon beams. FIG. 5 shows PDD curves for 2×2 cm 50 and 150 MeV electron beams compared to 6MV photons in a water phantom with 2 cm thick heterogeneous tissue at 10 cm depth, normalized to identical dose at 3 cm depth. As shown in FIG. 5, the 50 and 150 MeV VHEE beams are less sensitive to tissue heterogeneity over the density range from lung tissue to titanium prosthetic implants compared to 6 MV photons.

Figure 6:
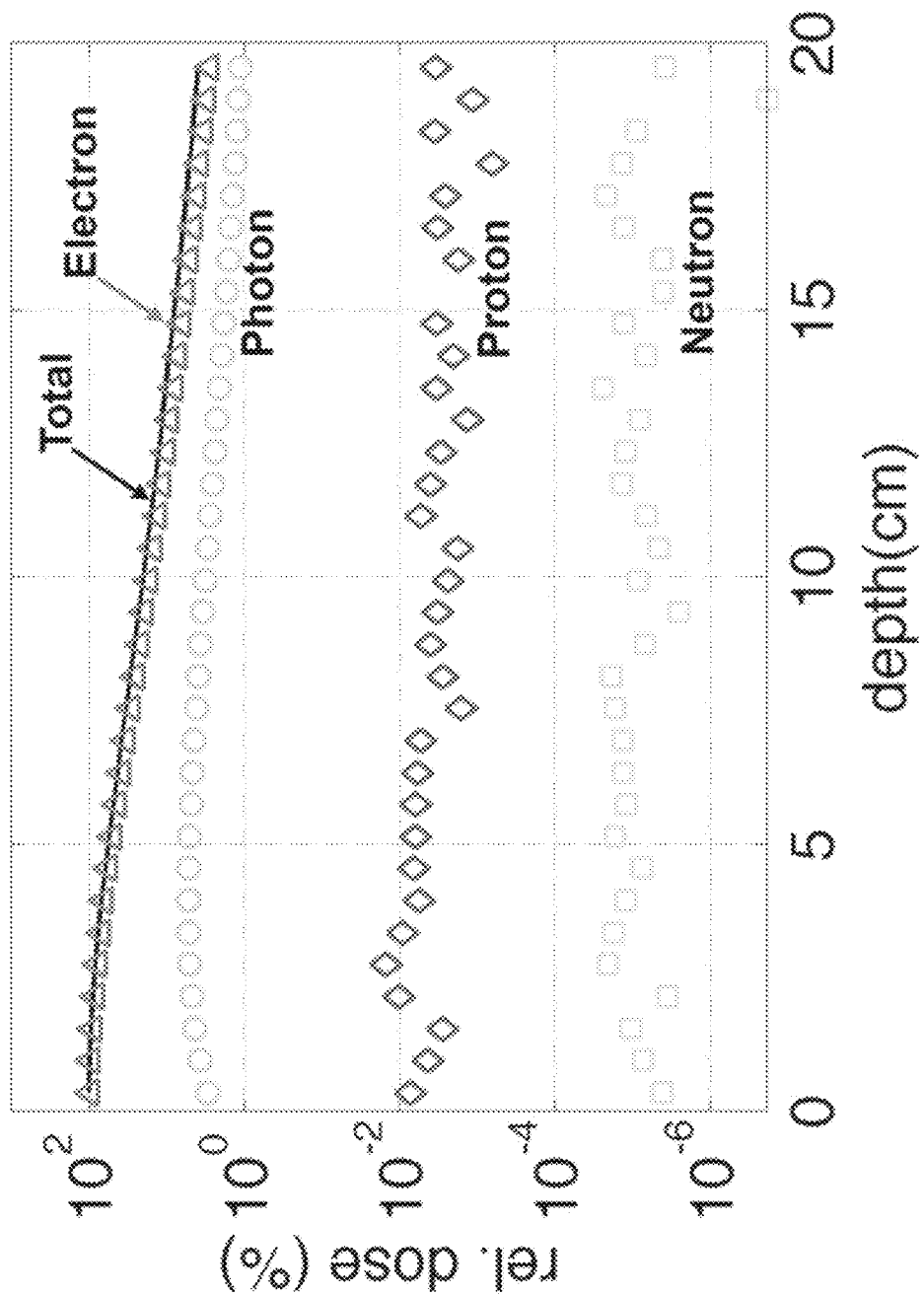
FIG. 6 shows graphic representations of relative contribution to dose from a 100 MeV electron beam vs. secondary generated particles (logarithmic scale).

Contribution of secondary particles produced by Bremsstrahlung and electronuclear interactions to the dose from VHEE beams were also analyzed. FIG. 6 shows relative contribution to dose from a 100 MeV electron beam vs. secondary generated particles (log scale). As shown in FIG. 6, for a 100 MeV electron beam, nearly all the deposited dose is due to electrons, with a minor contribution from Bremsstrahlung x-rays, and far lower dose from protons and neutrons. FIG. 6 also shows that dose from neutrons is far less than with 15-18 MV photons or high-energy protons. This holds for 50 and 70 MeV electrons as well (not shown). For a 25 Gy SABR treatment of a 2 cm diameter target, an upper limit of total body neutron dose is estimated to be 0.6 mSv based on MC simulations. This is in contrast to more than 1-2 orders of magnitude greater estimated neutron doses of 9-170 mSv for scanning beam proton therapy and 15-18 MV photon IMRT for the same clinical scenario, based on published measurements of ambient neutron doses [Schneider U, Agosteo S, Pedroni E, and Besserer J., "*Secondary neutron dose during proton therapy using spot scanning*," International Journal of Radiation Oncology Biology Physics, 2002; 53(1): 244-251. (PMID: 12007965); Howell R M, Ferenci M S, Hertel N E, Fullerton G D, Fox T, and Davis L W, "*Measurements of secondary neutron dose from* 15 *MV and* 18 *MV IMRT,*" Radiation Protection Dosimetry, 2005; 115(1-4): 508-512. (PMID: 16381776) both of which are incorporated herein by this reference]. An advantage of such potential designs according to certain embodiments compared to >8 MV photon and scanning beam or passive scattering proton therapies is elimination of need for beam modifying structures prior to beam incidence on the patient, in which most neutrons are generated with existing modalities.

d. Tissue Inhomogeneities

The effect of tissue inhomogeneities on dose deposition of VHEE beams has been studied by the inventors. A 20×20× 25 cm3 water phantom with 0.5×0.5×0.1 cm3 voxels and a 2-cm thick inhomogeneity placed at 10 cm depth was built (FIG. 7b). The 2-cm thick slab was consequently filled with lung with mass density ρ of 0.368 g/cm3, adipose (ρ=0.950 g/cm3), ribs (ρ=1.410 g/cm3), and cortical bone (ρ=1.920 g/cm3) tissue to assess the effect of human tissue inhomogeneities. The tissue composition was obtained from the ICRU-44 document [ICRU. Tissue substitutes in radiation dosimetry and measurement, 1989 (incorporated herein by this reference)]. Moreover, the effect of metals, such as hip prostheses, dental fillings, and surgical clips, was investigated by simulating a steel slab (ρ=8.030 g/cm3). Doses deposited by 50, 100, and 150 MeV electron beams, as well as 6 MV photon beam interacting with the inhomegeneity slab were simulated. The DOSXYZnrc code was chosen for this task due to its simplicity of use and its shortest calculation times. The statistical uncertainties in all central axis voxels were below 1%.

3. Ultra-High Gradient Accelerator Structure Design

Pluridirectional very high electron energy radiation therapy systems and processes according to various embodiments of the invention can be created with various types of electron source. There are a number of potential sources of very high-energy electrons in the range of, for example, up to about 250 MeV. A non-exhaustive list includes cyclotrons, synchrotrons, linacs (which can include more conventional designs with greater length), racetrack microtrons, dielectric wall accelerators, and laser plasma wakefield accelerator sources. Some of these are large and would need to be housed in a separate room. Some are not very mature technologies. In terms of goals of certain embodiments of the invention which can include any or all of compactness (entire system fitting within existing medical linac vaults without a separate room), power requirements, cost, repetition rates, compatibility with intensity modulation techniques described in this document, and other practical considerations, compact very high-gradient standing wave linear accelerators such as those developed at SLAC as described in the two paragraphs immediately below, or derivatives of them, may be at least a logical starting point, although other currently existing or future options should not be ruled out.

Highly efficient π-mode standing wave accelerator structures have been developed at SLAC for the project formerly known as the Next Linear Collider, a positron-electron collider at 500 GeV energy for high-energy physics research [Dolgashev V, Tantawi S, Higashi Y, and Spataro B, "*Geometric dependence of radio-frequency breakdown in normal conducting accelerating structures,*" Applied Physics Letters, 2010; 97(17). (http://apl.aip.org/resource/1/applab/v97/i17/p171501_s1) incorporated herein by this reference (hereinafter sometimes "Dolgashev 2010"). Such accelerators are capable of accelerating electrons to 100 MeV within 1 meter (Id.) using an optimized accelerating waveguide powered by a 50 MW 11.4 GHz microwave generator (klystron) [Caryotakis G. Development of X-band klystron technology at SLAC. Proceedings of the 1997 Particle Accelerator Conference, 1997; 3: 2894-2898. (http://ieeexplore.ieee.org/xpls/abs_all.jsp?arnumber=752852) incorporated herein by reference. In order to produce a practical system in terms of cost and size, optimized designs according to certain embodiments of the invention allow both economical production and high performance to minimize the treatment time while allowing maximum possible flexibility in beamlet shapes, directionality, and energy.

Furthermore, it has been shown that coupling a series of small sections of standing-wave accelerators with a distributed radiofrequency (RF) network makes it possible to design a system without any reflection to the RF source [Tantawi S G, "*rf distribution system for a set of standing-wave accelerator structures,*" Physical Review Special Topics-Accelerators and Beams, 2006; 9(11) (http://prst-ab.aps.org/abstract/PRSTAB/v9/i11/e112001) incorporated herein by this reference (hereinafter, "Tantawi 2006"). Building on these developments, practical implementations of a standing-wave accelerator structure have been designed to accelerate electrons to 100 MeV within one meter. (See for example, Neilson J, Tantawi S, and Dolgashev V, "Design of RF feed system and cavities for standing-wave accelerator structure," Nuclear Instruments and Methods in Physics Research A: Accelerators, Spectrometers, Detectors and Associated Equipment, 2011; 657(1): 52-54. (hereinafter, "Neilson 2011"), available online at (http://www.sciencedirect.com/science/article/pii/S0168900211008898), incorporated herein by reference). Such accelerators can serve as a basis for or be relevant to certain embodiments of the invention.

D. Other Design Issues

1. Design Options for the Injector System

To inject the required low charge bunch into accelerators according to certain embodiments of the invention, several possibilities are available. Those include a photo-injector RF gun. Additional options can be considered to reduce the cost and size of the system, including a variety of field emitter configurations and RF thermionic guns.

2. Optimization of the RF Source by the Addition of a Pulse Compression System

RF source requirements depend ultimately, at least in part, on the accelerator design. With the optimized cavities as described above, it is projected that a 50 MW source at X-band will be sufficient for a 2 meter accelerator operating at 50 MV/m. This type of source is available at SLAC and is being commercialized by Communications & Power Industries (Palo Alto, Calif.). With the use of a pulse compression system it may be possible to either reduce the cost and sophistication of the RF source dramatically or make the accelerator structure more compact by reducing the length to 1 meter. Because the typical filling time of such a structure is about 100 ns and the RF source typically provides several μs long pulses, one can use a compact pulse compressor with a high compression ratio and a power gain of about 3.5 to reduce the required RF source power to only about 14 MW, which opens the door for a variety of sources, including sources that are commercially available now, and including those that include a pulse compression system.

3. Imaging and Target Position Verification Options

Given that treatment according to certain embodiments of the invention is delivered sufficiently fast to freeze physiologic motion, it is important to verify that the target is in the planned position at the time the treatment is triggered or administered. Several dynamic or "real-time" imaging or other localization technologies can be integrated into certain embodiments of the invention for this purpose. Potential such implementations can include any of the following, alone or in combination:

a. Integration of two or more x-ray fluoroscopic imaging devices, forming at least one orthogonal pair, to permit real-time 3-dimensional verification of alignment of bony anatomy and/or implanted radio-opaque fiducial markers.

b. Dynamic optical surface scanning, ideally combined with an internal imaging modality such as CT or fluoroscopy, providing real-time correlation of the external surface to the internal target position.

c. Integration of fast x-ray computed tomography. This can be accomplished by the addition of a relatively conventional multi-detector CT system within the gantry of the treatment system. Alternatively, if a continuous ring gantry design is used for the treatment delivery system, the treatment system itself can be used to scan a low energy (around 100 keV) electron beam across a ring-shaped target introduced into the beam path to produce a rapidly moving x-ray source for very fast CT scanning, known as "electron beam CT" immediately before switching to the high energy treatment beam.

d. Implantable radiofrequency beacons, whose 3-dimensional position can be read out in real time by an external antenna array. Beacons can be implanted in or near the target and serve as surrogates for the target position.

e. Integration of ultrasound. For certain anatomic locations, for example the upper abdomen and pelvis, ultrasound can provide continuous real-time 3-dimensional localization of targets.

f. While the most technologically complex to implement, magnetic resonance imaging may be implemented, which can provide real-time 3-dimensional localization of targets. Integration of MRI with conventional photon therapy systems is already commercially available or under development by multiple vendors.

In any of these implementations, dynamic visualization and/or automated image analysis tools can be used to permit either manual triggering of the treatment by the operator, or automated triggering with manual override.

4. Implementation of Intensity Modulation

According to certain embodiments of the invention, which may be used with various types of accelerators in accordance with the invention, and in order to achieve highly conformal volumetric dose shaping, radiation fields from each of multiple beam directions can cover an area with varying beam intensity across the field, with the intensity patterns optimized to produce the desired 3-dimensional dose distribution when summed across all beam directions. Such intensity modulation may be produced by raster scanning individual beamlets of varying intensity across the field from each beam direction. Alternatively, it may be produced by using a 2-dimensional intensity-modulated electron pattern at the source, effectively an array of beamlets of varying intensity, and accelerate and steer the entire array to the target volume. This eliminates the need for a raster scanning mechanism at the exit of each of the beam channels, greatly simplifying the design and reducing the bulk and cost of those components, and increases the treatment delivery speed by delivering beamlets in parallel within a much smaller number of electron pulses or bunches.

II. Technologies to Facilitate Radiation Delivery in Rapid Radiation Treatments

A. Photo Cathode/Photo Electron-Gun

In accordance with certain aspects, methods and systems for rapid generation and delivery of transversely patterned electron beam to targeted tissue for rapid radiation treatment utilize a photo-electron gun. A photo-electron gun is one of various possible techniques that may be used for precise and ultrafast dose delivery using a medical electron accelerator in accordance with the present invention. The dose is produced in rapid pulses of electrons delivered to the targeted tissue from different directions, different transverse beam pattern in each direction. Each pulse has a pre-programmed transverse dose pattern such that the total 3D dose conforms to the target volume in the patient. Projecting a pre-programmed light pattern on a photocathode generates replica of this light pattern with similar transverse distribution of the electrons. This pattern or image is then accelerated through low aberration electron optics toward the targeted tissue.

According to some embodiments, the intensity modulation of the electron source may be produced by using a photocathode illuminated by a light source with the corresponding intensity pattern, in effect, an optical image. One implementation is to use a laser as the light source, and a digital light processing (DLP) micromirror array or other intensity modulating device to produce the charge image on the photocathode to be accelerated and steered. The electron beam optics can be designed to maintain the pattern with high fidelity until it reaches the target.

Figure 8:
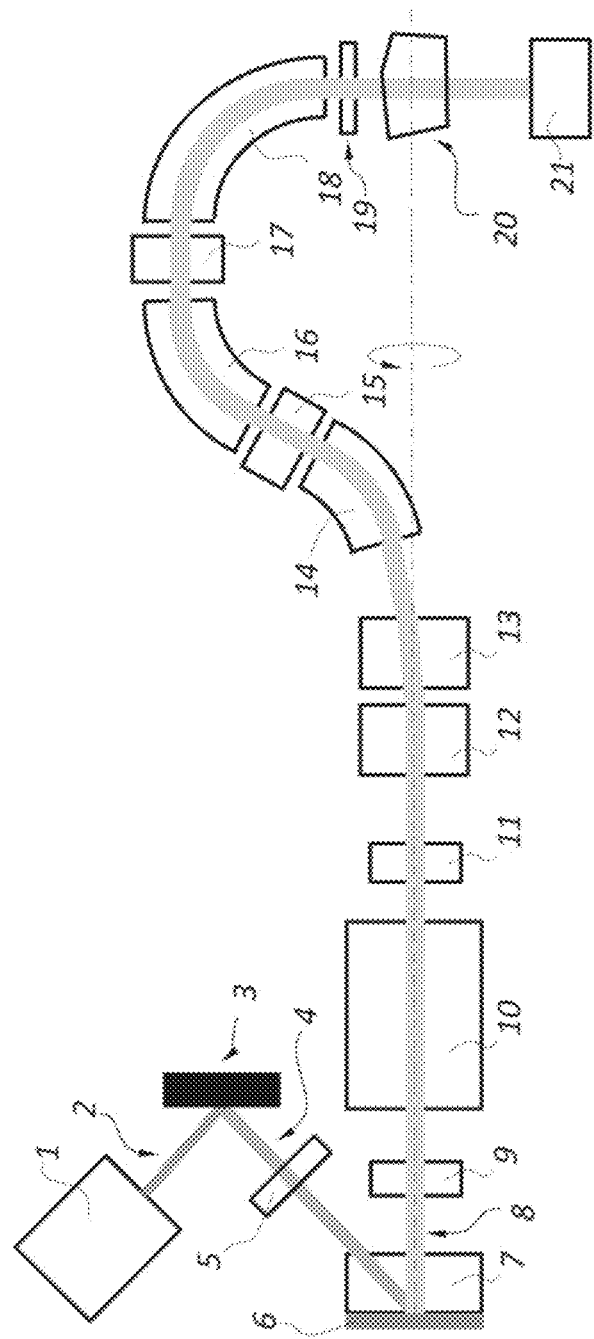
FIG. 8 schematically shows portions of a radiation treatment system with modulation of electron beam transverse profile using pulse-to-pulse modulation of injection laser beam profile impacting a photocathode of an electron injector.

According to one nonlimiting embodiment as shown in FIG. 8, a short, typically picosecond-long pulse with uniform transverse profile is generated by a laser (1). The wavelength of the laser is matched with specific photocathode material to obtain required charge and emittance. The laser pulse (2) falls on a digital-micro-mirror device (3). Pixels of this micro-mirror device are controlled by a computer and will reflect a portion of the laser pulse (4) thus creating an image that is then transferred to the photocathode (6) using precision projection optics (5). Although various types of accelerators may be used with this embodiment, high gradient pulsed devices with a few milliseconds between pulses are preferable. The computer modulates the mirror array thus creating a new image for each consequent pulse. A laser pulse with amplitude-modulated transverse profile that impacts the photocathode (6) will create an electron replica of the laser pulse transverse profile (8). The photocathode (6) is a part of photo-electron gun (7). The gun creates an electric field on the photocathode which accelerates the transverse-modulated electron beam. The gun also provides initial focusing for the electron beam. The electron beam then passes through the low-aberration focusing system toward accelerator (10). The accelerator increases energy of the beam to a desired value. The electron beam then passes through focusing optics (11) toward horizontal (12) and vertical (13) fast deflectors. The deflectors are controlled by a computer and are able to send the electron beam in different directions for each consecutive accelerator pulse. The desired direction will depend on (among other things) specific realization of the gantry's beam lines, number of the beam lines and whether they are movable or not. For clarity only one gantry beam line is shown in FIG. 8. After the deflectors, the electron beam passes through bending magnets (14, 16, 18) and electron optics (15, 17) and is directed through electron-beam monitoring system (19) toward the target (20). The transversely modulated electron beam irradiates the target with required distribution of the dose. After passing through the target, the beam is sent toward beam dump (21) in order to reduce unwanted radiation exposure of the target.

Of note, a greater degree of intensity modulation will produce more conformal dose distributions. However, with conventional photon therapy where intensity modulation is delivered in a serial fashion over time, more modulation comes at a cost of longer delivery time, more leakage dose to the patient, and greater uncertainty in delivered dose because of target and organ motion during the longer treatment delivery time and its interplay. With VHEE technology according to certain embodiments of the invention, all of these problems are circumvented: arbitrarily complex intensity modulation can be produced through optical imaging, and rapid parallel delivery eliminates uncertainty from interplay effects.

The concept of conversion of an optical intensity pattern into a radiation intensity pattern within a patient is considered to be unique, and also uniquely applicable to electron beam therapy in accordance with embodiments of the invention as opposed, for example, to photon or proton or other particle therapies. In certain aspects, the light-pulse generation could be based on laser, light-emitting diode, or various other light sources with power, wavelength, and pulse length optimized to produce sufficient electron charge and initial emittance from a specific photocathode material.

B. Array of Accelerating Structures

In accordance with certain implementations of the present invention, one or more RF power supplies (ideally compact), including low voltage multi-beam klystrons, provide efficient radiofrequency power that is distributed to an array of electron accelerating structures through a multi-port phased array microwave network. These technologies can be used to apply radiation therapy using conventional therapeutic electron beam energies (1-20 MeV) with or without conversion to high-energy photons (x-rays), as well as very high-energy electrons (up to 250 MeV). When treating with photons, scanning of an electron beam across a stationary bremsstrahlung target and collimator array eliminates the need for mechanical collimator motion. An electron gun that produces a two-dimensional transverse intensity-modulated electron beam and beam optics to propagate this pattern through the accelerator to the target in the patient can be used to replace raster-scanning mechanisms. The system integrates imaging of sufficient speed and quality to permit real-time treatment planning and position verification and treatment delivery all within the specified time frame or alternatively may be used to apply a pre-determined treatment plan using real-time imaging. Variations of the design are discussed in further detail below.

One way to increase the speed of radiation delivery is to direct beams to the targeted tissue from multiple directions in rapid succession or nearly simultaneously through an array of accelerating structures rather than by mechanically rotating or moving a single linac source around the patient. This configuration is generally not practical if the typical high-power radiofrequency (RF) power source (eg, a klystron or magnetron) must be replicated multiple (N) times, requiring N high-power sources for N accelerator structures. These challenges can be overcome by use of the following innovations described in PCT Application No. PCT/US2014/055260.

Figures 1, 9A:
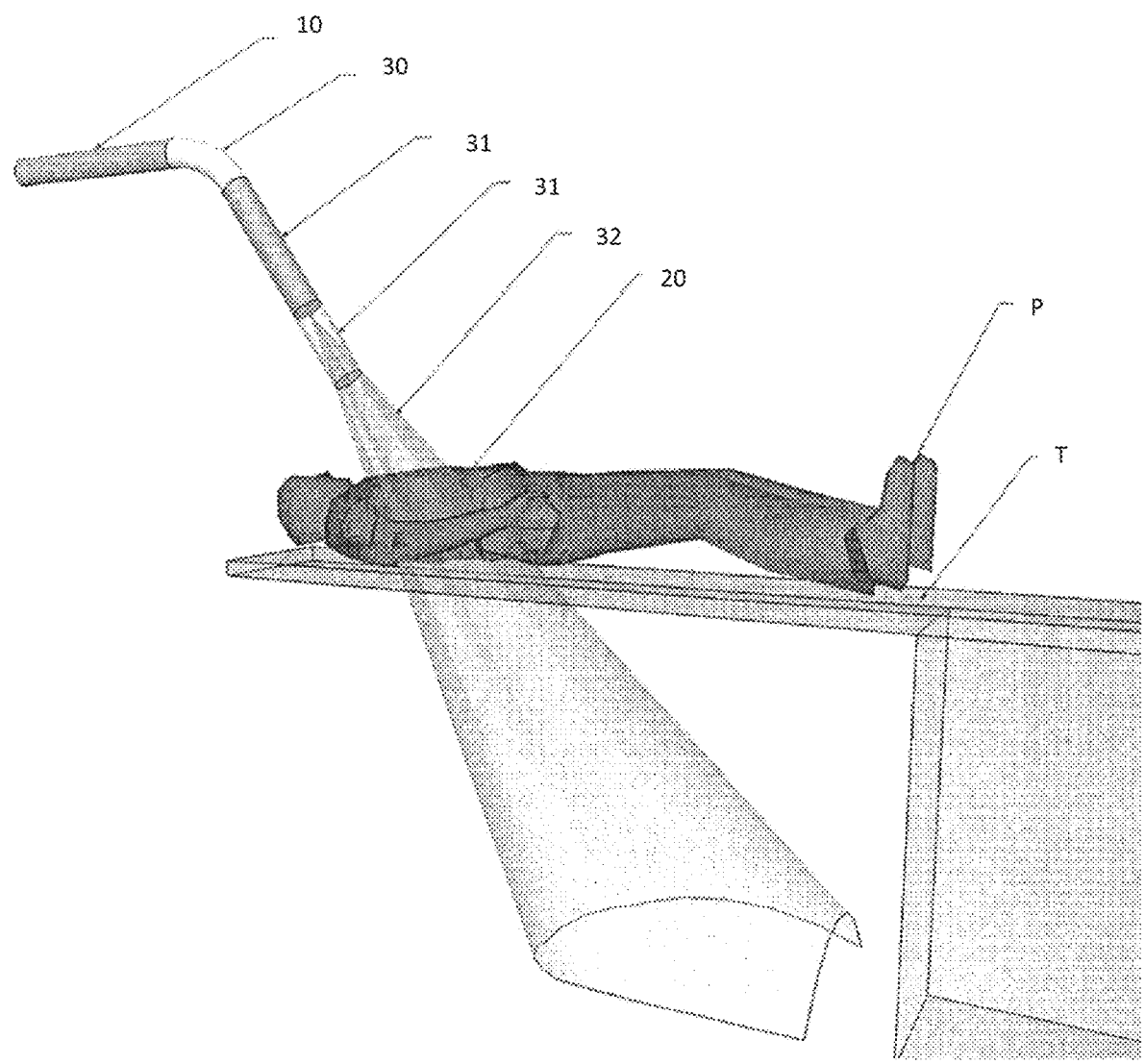
Figures 2, 9A:
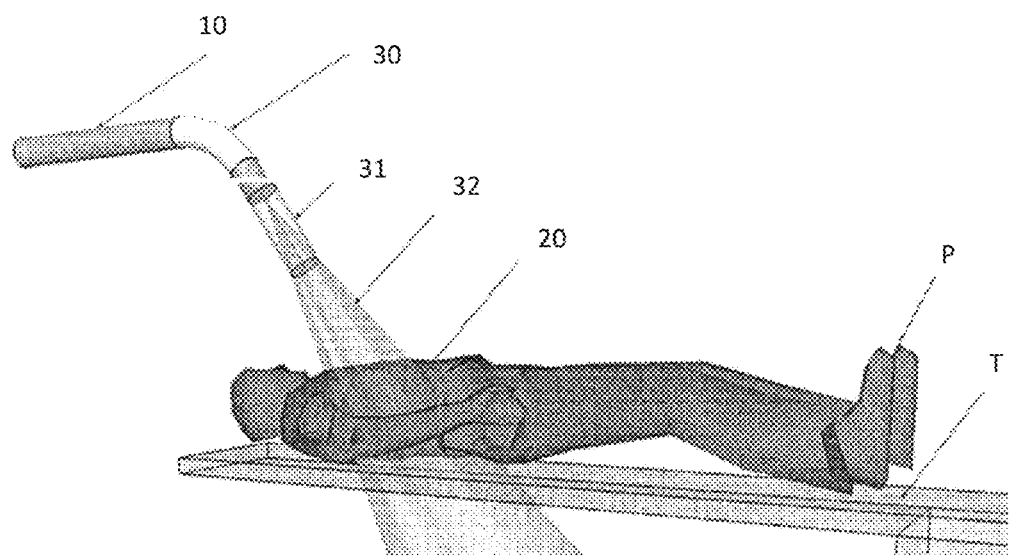
Figures 3, 9A:
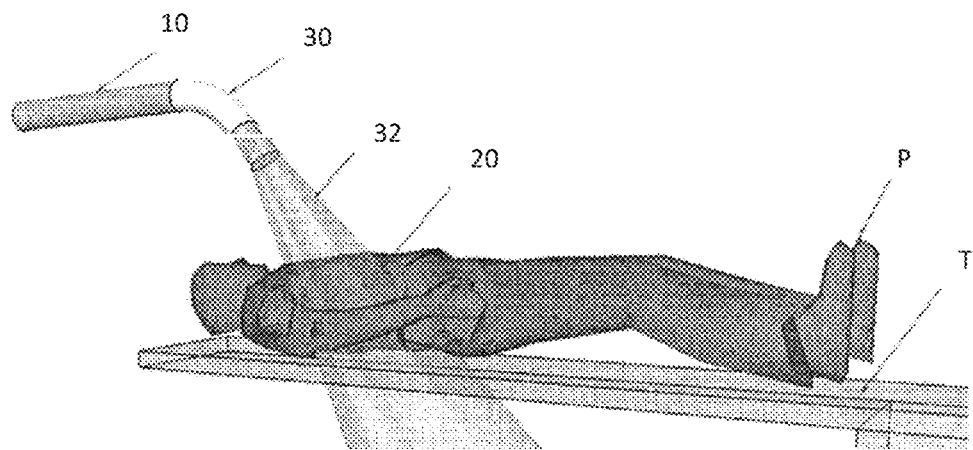

FIG. 9A-1 shows one possible beam line geometry that may be used in a multi-beam system. FIG. 9A-1 shows the components of an individual beamline, which includes a first accelerating structure 10 extending along a horizontal axis substantially parallel to a longitudinal axis of the table T on which the patient P lies during treatment. Next, the beam is steered by a bending structure 30 toward the patient P, such as by one or more steering magnets such that steering is performed without movement of any mechanically moving parts. Typically, the steering portion 30 is a non-accelerating portion of the beam line and may this portion may also include one or more focusing optics so as to maintain certain properties of the beam during steering. Next, the beam is accelerated further in a second accelerating portion 10 angled toward the patient P. The beamline may also include a treatment head 31 in which the beam may be adapted according to a particular treatment pattern or any existing pattern may be verified before the treatment beam 32 is delivered to the targeted tissue 20. In some embodiments, the treatment head may a photo source or collimator so as to generate a photon beam for delivery to the targeted tissue. In some embodiments, such as that shown in FIG. 9A-2, the beamline includes a single accelerating structure 10 after which the beam is bent in a single steering portion 30 before being magnified and directed to the target tissue. Such embodiments may include a treatment head 10 as described above positioned just downstream of the steering portion. The steering portion 30 includes one or more steering device and is configured to effect steering of the beam toward the target tissue after the beam has reached full acceleration. In other embodiments, such as that shown in FIG. 9A-3, the beamline may include a singled accelerating portion 10 and a steering portion 30 in which the beam is magnified concurrently with steering. A treatment may also be used with this embodiment. The embodiments in FIGS. 9A-2 and 9A-3 allow further reduction in size of the array. It is appreciated that a system in accordance with aspects of the invention may include an array of beamlines of various different configurations, including but not limited to any of those described herein.

Figure 9B:
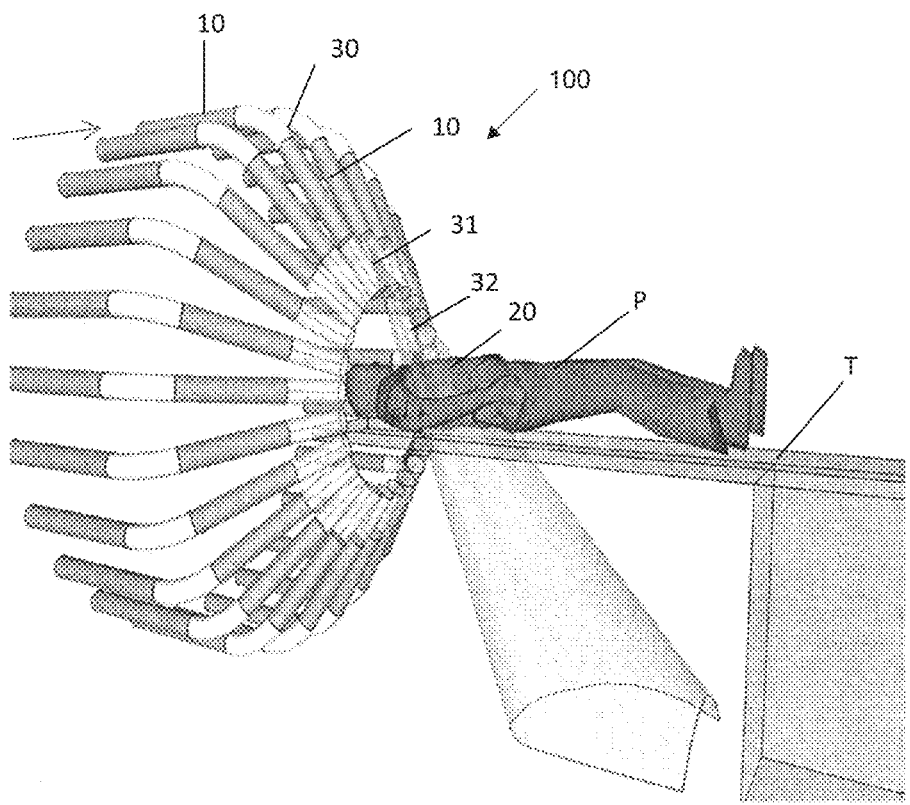
FIGS. 9B-9D illustrate a rapid radiation system having an array of accelerating structures and an imaging system in accordance with certain embodiments.
Figure 9C:
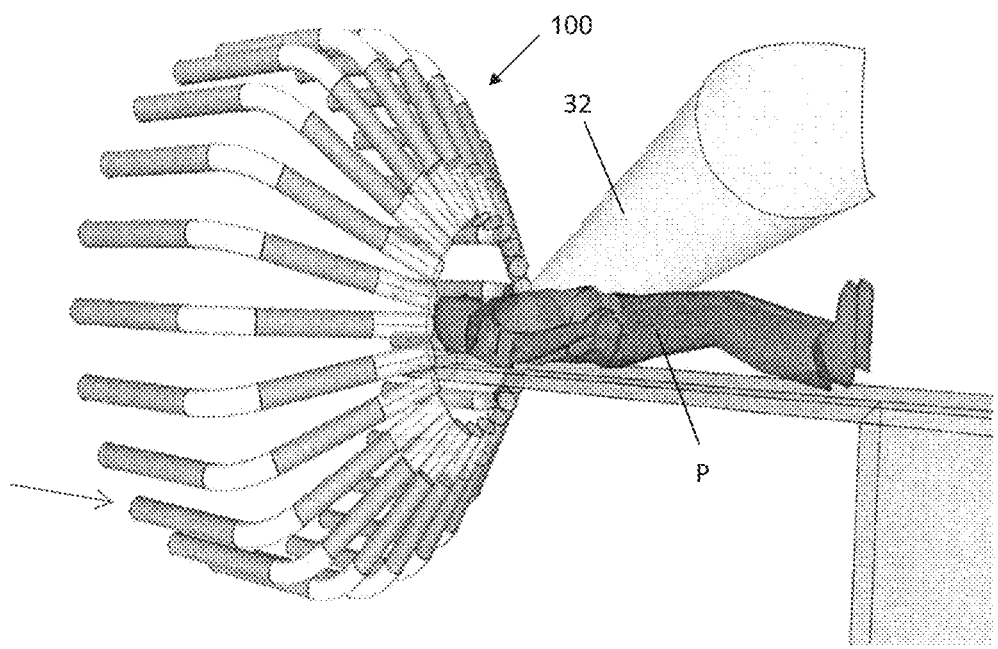
Figure 9D:
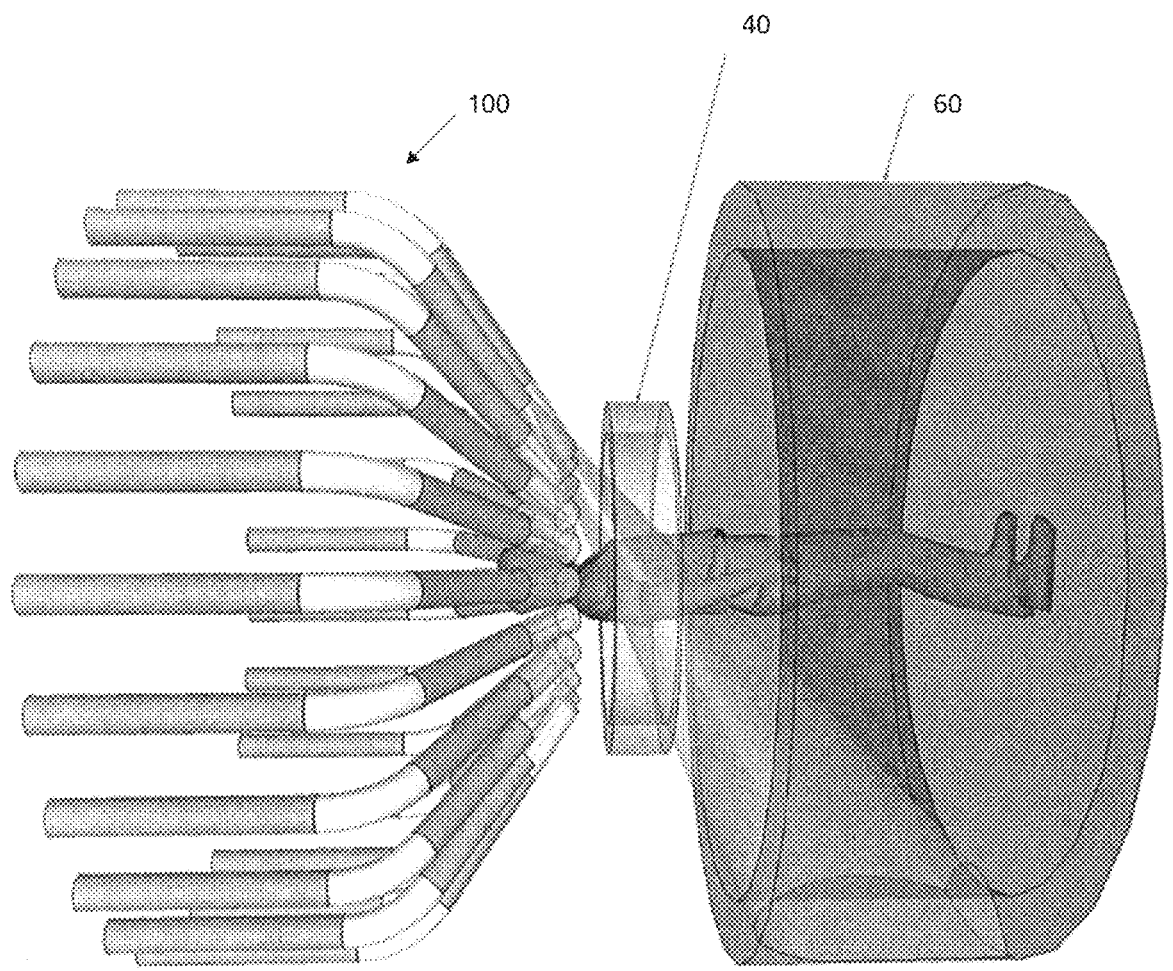

FIG. 9B shows a configuration of multiple beamlines around the patient (25 in this example) arranged in an array of accelerating structures 100. In this embodiment, the accelerating structures are disposed in a radial array about a longitudinal axis extending through a common target through which each beamline extends and at which the targeted tissue is positioned. In one aspect, each of the accelerating structures of the radial array are substantially identical to readily facilitate rapid delivery of multiple beams through select accelerating structures of the array (shown by arrows) in rapid succession and/or simultaneously to the targeted tissue at the common target. This approach allows particle beams of differing intensity and shapes to be directed to the targeted tissue from multiple directions so as to provide vastly improved conformance with a targeted tissue, such as a tumor. The beamlines are activated rapidly in sequence to direct beams to the patient target zone from different directions (see for example FIGS. 9B-9C). Advantageously, this may be performed rapidly enough to deliver an entire radiation treatment dose to the targeted tissue in less than 10 seconds, often in a few seconds or less, even within a second or less. It is appreciated that less than all accelerating structures may be used in a particular treatment. For example, depending on the application and the targeted tissue, delivering treatment through select accelerating structures, such as through a majority of the structures or through only a few structures, may be sufficient. Rapid radiation delivery is facilitated by a rapid imaging system. Such a system may be integrated within the treatment system. FIG. 9D shows the integration of a full-ring volumetric imaging system 40, and a primary beam stop 60 that may be necessary for very high-energy beams. The radial array configuration and acute angle at which the accelerating structures extend towards the common target allow for the depicted placement of the imaging system and beam stop shown in FIG. 9D. In certain embodiments, the system may include any of the configurations in the following examples described below.

In one example, the treatment beams may consist of conventional energy electrons (up to approximately 20 MeV) for treatment of superficial targets in the patient. In this variation, the accelerator structure will have maximum energy in the range of conventional medical linac systems. Each treatment head would provide a means of spatially modulating the beam. One of the most rapid ways to do this would be by electromagnetic rastering of a pencil beam, or by using a transverse intensity-modulated electron source (further described in section 4). Slower alternatives would include electron multi-leaf collimators (MLC) or conventional static blocks or compensators. Static blocks or compensators are not compatible with adaptive or real-time replanning.

In another example, the treatment beams may consist of conventional energy photons (up to approximately 20 MV) for treatment of deep-seated targets in the patient. In this variation, the accelerator structure will have an accelerating gradient in the range of conventional medical linac systems, but much higher average current in order to achieve very rapid delivery. Each treatment head would provide a means of collimating and spatially modulating the beam. Among the more rapid ways of accomplishing this would be by electromagnetic rastering of an electron pencil beam, or by using a transverse intensity-modulated electron source (further described in section 4), and converting the electrons to photons using a bremsstrahlung target and collimator grid combination (further described in section 5). Alternatives include using conventional photon MLCs and static or dynamic compensator-based intensity-modulators. Static compensator-based intensity-modulators are not compatible with adaptive or real-time replanning.

In yet another example, the treatment beams may consist of very high-energy electrons (VHEE) (approximately 50-250 MeV) for treatment of deep-seated targets in the patient. In this variation, the accelerator structures will have an accelerating gradient substantially higher than those of conventional medical linac systems to allow compactness. In this variation, there are various advantages to having an additional accelerator structure in each beamline. For example, one advantage is that allowing for a longer total length of accelerating waveguides and thus a lower accelerating gradient and power requirement than for a single accelerator structure within the same total space. Another advantage is that bending the beam can occur before it reaches the full energy and thus lower field bending magnets can be used or sharper bending can be achieved for the same bending magnet field. Yet another advantages is that producing a broader range of beam energies within the same device, since the additional accelerator structure could also be used to decelerate the beam to produce lower energy electron beams in addition to accelerate the beam to produce the highest energy beams. Each treatment head may provide a means of spatially modulating the beam. This would be accomplished by electromagnetic or RF deflection rastering of a pencil beam, or by using a transverse intensity-modulated electron source (further described in section 4). In this variation, a primary beam stop is included to minimize generation of very high-energy bremsstrahlung and secondary particles (e.g., neutrons) from the exiting VHEE beam.

In some embodiments, the treatment beams may be arranged in a conventional coplanar configuration. In other embodiments, the treatment beams may be arranged in a non-coplanar configuration. An example non-coplanar configuration is illustrated in FIG. 1. There are various advantages of using non-coplanar beams. One advantage is that such a configuration would leave room for a full coplanar imaging system, such as CT or MRI (additional imaging options are described in section 6). Another advantage is that such a configuration may provide an option for a simple primary beam stopping geometry, which may be necessary for very high-energy beams, and may also provide more room for accelerator structure length and/or allows less acute bending of the beam, both of which are more important as the beam energy increases. In another aspect, dose conformity may be improved, especially at low-intermediate dose levels, with a more isotropic dose falloff with distance from the targeted tissue. The patient axis may be horizontal or vertical, and the beamlines oriented accordingly. In the case of conventional energy electron and photon therapy, there is no need for a primary beam stop, in which case there would be more room for the imaging system and/or additional beamlines.

In one aspect, any number of beamlines could be used subject to space and cost constraints. When combined with the phased array power distribution network described in section 2, it may be particularly useful to use a square number of beamlines would (eg, 4, 9, 16, 25, 36, 49, etc.). If the number of beamlines is cost-limiting, a few beamlines or even a single beamline could be rotated around the patient on a gantry at sufficient speed to complete the treatment within the specified time frame. The larger the number of beamlines, the lower the rotational speed required for a given treatment time. With a sufficient number of beamlines (approximately 9 or more), the incremental dosimetric benefit of employing mechanical rotation diminishes to the point of not justifying the complexity. In some embodiments using electron beams, acceleration may be accomplished with a single accelerating structure or a small number of them, and the beam(s) subsequently steered to multiple treatment heads around the patient.

Figure 13A:
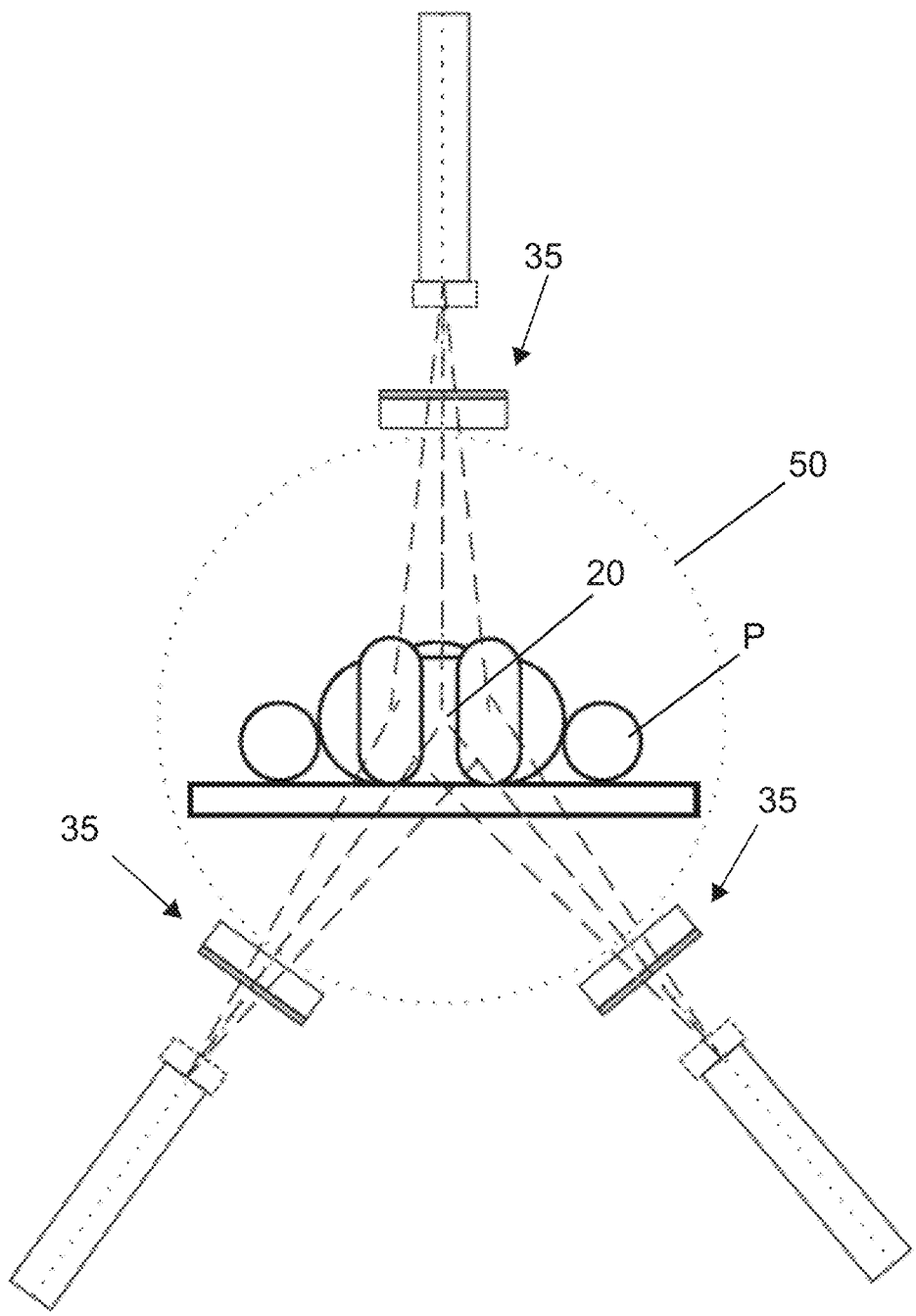
FIG. 13A shows a schematic of a treatment system having a rotating gantry or fixed assembly that includes multiple beamlines with or without collimation assemblies, in accordance with aspects of the invention.

In one aspect, the system may include a rotating gantry 50 having one or more beamlines and collimation assemblies 35 thereon so as to allow collimated beams from multiple differing directions. In some embodiments, a rotating carousel may be used include one or more collimation assemblies 35 or multiple collimation assemblies with differing geometries. FIG. 13A shows an example of coplanar beamlines perpendicular to the patient, in which there are multiple beamlines, or in the alternative, FIG. 13A may represent a single or a few beamlines and a rotating gantry 50 supporting multiple beamlines and collimation assemblies affixed thereon. Of note, a collimation assembly, such as the SPHINX collimation structure may, be used together with conventional energy electron linacs (up to ~20 MeV). In some embodiments, the beamlines may utilize transport/magnifying optics rather than a SPHINX collimation structure. Rotation of the gantry allows the beamlines and collimation assemblies to direct beams toward the targeted tissue from different directions as needed. In some embodiments, rotation of the gantry would be a requirement if the number of beamlines is small (for example, less than seven beamlines). In addition, these aspects may apply to a system in which the beamlines are noncoplanar and at an oblique angle to the patient axis.

Figure 13B:
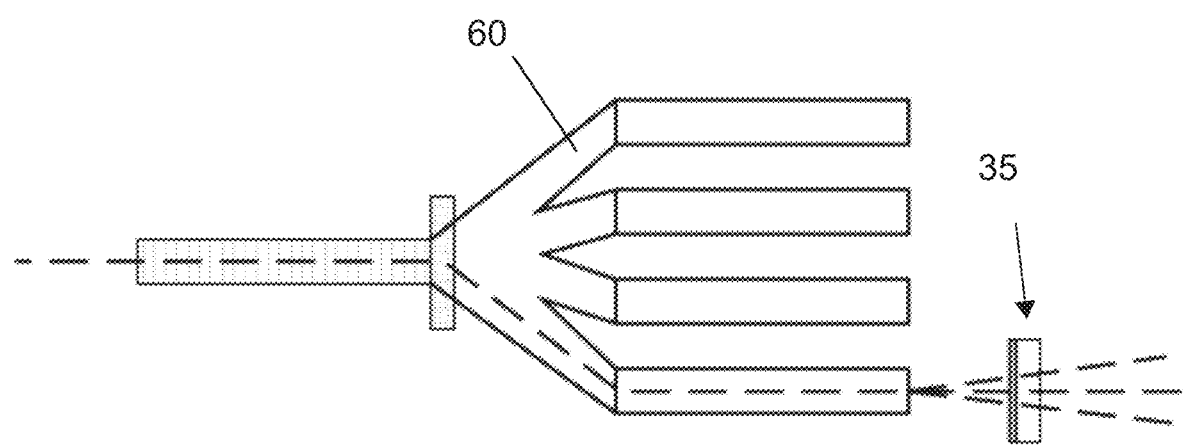
FIG. 13B shows a treatment system having multiple beamlines from a single accelerator for use with or without a collimation assembly, in accordance with aspects of the invention.

FIG. 13B illustrates a schematic of an example system where a single electron linear accelerator feeds multiple beamlines (four beamlines in this example) in a multi-beamline structure 60. A beam deflecting device may be configured to move the beam between the different beamlines. Each beamline may be used with a collimation assembly, such as a SPHINX structure, (only one being shown in FIG. 13B) if the appropriate energy range, or the beamlines may be used without a collimation assembly such as in a very high energy electron beam treatment.

In one aspect, a system includes one or more treatment heads, each having a suitable collimation assemblies disposed within for use in a radiation treatment of a targeted tissue in a patient. In some embodiments, the one or more treatment heads are coupleable with any of a set of collimator assemblies having different shapes and/or geometries, such as any of those described therein, which are selected by a user as desired for a given treatment. In some embodiments, the system includes a rotating gantry having multiple differing collimating assemblies such that selection of a particular collimating assembly can be effected by rotation of the gantry. In another aspect, the collimating assemblies can be removable from the treatment heads such that the desired collimating assemblies are selected and attached to the treatment heads in preparation for the procedure.

It is further appreciated that the above described features relating to an array of accelerating structures may be used in various other radiation treatment systems, including those with radiation delivery time scales greater than the reduced delivery times associated with rapid radiation treatments.

C. Imaging Strategies for Extremely Rapid Radiation Therapy

In accordance with certain embodiments, the treatment system utilizes an imaging system configured to obtain and provide imaging information sufficiently fast to allow radiation delivery to the targeted tissues with improved accuracy within the time-scales described herein. Although the imaging systems and methods are particularly advantageous when used with a rapid radiation treatment system, such as any of those described herein, it is appreciated that any of the aspects described below may be applied to various other radiation treatment system, as well as various other medical or non-medical systems or processing benefiting from improved imaging.

In certain aspects, a treatment system in accordance with embodiments of the present invention include an imaging system configured to provide rapid radiation therapy using a high-energy electron beam. In accordance with this aspect, the imaging system embodiments can be divided into the three categories described below. It is appreciated that the following categories are not exclusive and further that the examples listed within each category are merely illustrative of various concepts and do not limit the invention to those particular examples.

In one aspect, the invention provide method of verifying patient position relative to the radiation therapy treatment system by using one or more VHEE beam(s) to provide 'low energy' photons. It is possible to 'detune' the accelerator such that electrons are produced within an energy range of interest for x-ray imaging, such as within a range of about 20 keV to about 6 MeV. For example, in embodiments in which two linear accelerators are applied to accelerate a single electron beam, the two accelerators could be tuned so that the first accelerator accelerates the electron beam while the second accelerator decelerates the electron beam. A high-Z target may be placed in front of the electron beam, between the exit nozzle of the beam and the patient, would then produce a diagnostic-energy x-ray beam with a focal spot size on the order of the electron beam diameter, such as 5 mm or less, typically less than 2 mm. Such diagnostic-energy x-ray beams may be used to acquire images of the patient that demonstrate soft-tissue, bony structures, contrast-filled vessels, fiducial markers and the like.

In some embodiments, such an electron beam can be moved in a rastered fashion to provide focal spots at many locations. The high-Z target could be combined with appropriate collimation to limit the exposed region of the patient to the imaging region of interest.

In another aspect, the system may include a corresponding multi-row ring of x-ray detectors (stationary or rotating, single detector, multiple detector, single row, multiple row) configured to detect the photons. The resulting images could be viewed as projection images, or could be combined (reconstructed) to provide 3D CT-like reconstructions of the patient. Given the 'few view' nature of the acquired data, which is likely less than 100, reconstruction would likely be achieved using iterative reconstruction or sparse reconstruction algorithms. Prior CT or other 3D images, such as MRI, PET/CT, SPECT, PET, ultrasound images, of the patient acquired on the same day or on a different day prior to or after the treatment could be used to constrain the reconstruction and improve the 3D image quality.

In some embodiments, the imaging system used to obtain the treatment image immediately before treatment is also configured to obtain the patient images prior the treatment for use according to the above methods. Such a treatment system may include one or more suitable imaging devices, including combinations of differing types of imaging or may rely primarily or solely on CT scanning, such by use of the integrated CT imaging ring shown in FIG. 9C. Same or similar approaches may be used with stationary (fixed angle) accelerators, accelerators mounted on a rotating gantry, or the steering electron beam configuration such as those shown in FIG. 1 and FIGS. 13A-13B, with appropriate modification of the high-Z target and collimation system as necessary.

In one aspect, the system may include an active cooling feature of the target, for example air or water cooling, or other suitable active cooling features as would be known to one of skill in the art. Active cooling of the target could be provided to increase x-ray output. The high-Z target could be a transmission target or a reflection target, which may comprise a solid or a liquid.

Of note, a non-coplanar arrangement of beams (for example as illustrated in FIG. 9D) allows for the integration of a full ring imaging system (eg, CT, MRI, PET, or combinations thereof) that provides images of diagnostic quality and speed. This applies to radiation therapy in general beyond PHASER.

1. Category 1: Patient/Lesion/Soft-Tissue/Fiducial Position Verification, to Permit Planning/Replanning/Plan Selection Prior to Therapy Delivery. The Imaging Task Should Completed in <20 s.

These aspects can be further understood by reference to the following examples. In a first example, the imaging system may be integrated permanently into the radiation treatment system; a single imaging system or multiple integrated and cross-calibrated imaging systems (see FIG. 9D and FIG. 10 for one example of system with cylindrical geometry integrated into the system). In a second example, a 'large' imaging system on rails (e.g. MRI, CT) with accurate re-positioning and/or real-time tracking of two (or multiple) coordinate systems moveable relative the radiation treatment system. In a third example, a 'large' imaging system (e.g. MRI, CT, PET/CT) with patient table motion between the radiation treatment system and the imaging system with accurate re-positioning and/or real-time tracking of two (or multiple) coordinate systems. In general, for each imaging techniques, a method/phantom/validation for cross-calibration between electron delivery system and imaging system geometries are obtained.

Figure 10:
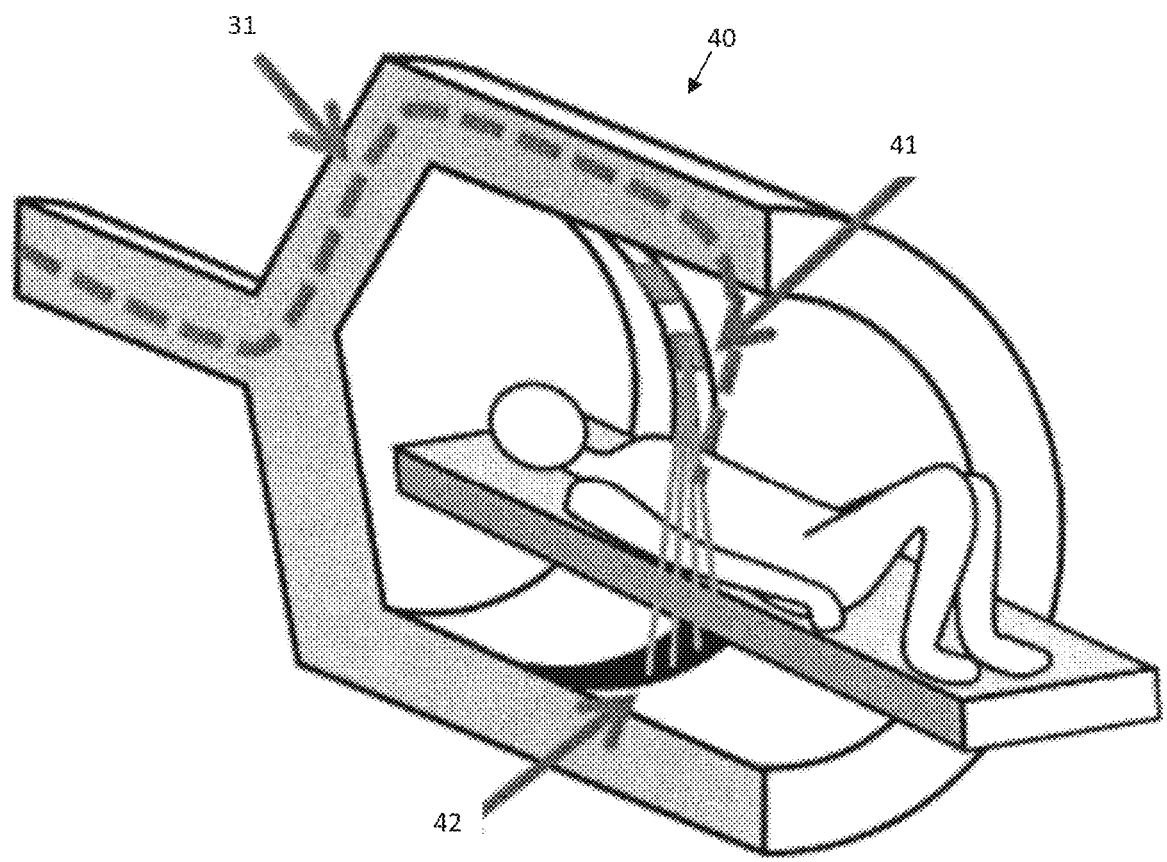
FIG. 10 illustrates a rapid radiation treatment system having an imaging system utilizing an array of x-ray sources and detectors.

While in many embodiments the imaging system is described for use with a treatment system having an array of accelerators, it is appreciated that such an imaging system may be used in any rapid radiation treatment system. FIG. 10 illustrates an imaging system in accordance with aspects of in the invention used in a system having a gantry with multiple beam ports through which beams are steered from differing directions, similar to that shown in FIG. 1. In FIG. 10, the imaging system 40 may include a ring of imaging devices incorporated into the gantry itself, the ring device having a 180 degree array of x-ray sources 41 and a 180 degree array of x-ray detectors 42 in an opposite side of the gantry. This detectors may be offset along a longitudinal axis along which the patient lies (x-ray sources and detectors being positioned on opposite sides of the ring of beam ports through which the treatment beams extend) such that the x-rays pass directly through the targeted tissue. In some embodiments, a similar ring may also be included on alternate side of the ring of beam ports in reverse, that is the x-ray sources being disposed under the patient (on a side of the ring of beam ports closer the patient's head) and the x-ray detectors being disposed on the upper half of the gantry (on a side of the ring of beam ports closer the patient's feet), while in other embodiments the sources and detectors are not offset.

In one aspect, the imaging system may use of x-ray or magnetic field based systems and may include various contrast enhanced techniques, imaging processing aspects, and motion management/motion tracking, or various combinations thereof. Examples of each of these aspects are provided below. It is appreciated, however, that these examples are merely illustrative and the system is not limited to any of those aspects detailed further below.

In some embodiments, X-ray based imaging systems may include use of computed tomography, tomosynthesis, bi-plane x-ray imaging, phase contrast x-ray imaging or various x-ray imaging systems. Computed tomography may include a stationary array of x-ray sources (1D or 2D) with rotating detector, single or multi-row detector; a standard rotating CT system geometry; or a tilted rotating CT system geometry. Tomosynthesis may include a stationary array of x-ray sources (1D or 2D) with stationary array of detectors, with 'limited' angular coverage, could be as high as 180.° Bi-plane x-ray imaging may be included, likely in conjunction with placement of fiducials, or for tracking of boney landmarks. Systems may include use of an X-ray target, cathodes and any of various detectors. X-ray targets may include: Reflection, transmission, stationary anode, rotating anode targets, etc. of several different materials e.g. W, Mo, Rh. Cathodes may utilize a standard filament, a condenser, a carbon nanotube cold cathode, or a scanning electron beam. Various other detectors may include standard detectors, photon-counting detectors, energy-discriminating detectors, detectors that convert x-ray signal to optical (e.g. $CdWO_4$, direct detection e.g. $HgI_2$;); backplane electronics from amorphous silicon, rad-hard CMOS, curved detector, flat detectors.

In magnetic-field based imaging systems, imaging may be performed utilizing various different aspects. In one aspect, such systems may utilize a standard, superconducting MRI system that fits within the confines of the radiation treatment system or is added to the back end of the system. The field strength could be from 0.25 T-3 T. Imaging techniques include but are not limited to standard T1, T2, T2*, perfusion, diffusion, parallel transmit and receive, spectroscopy, spectroscopy of Brownian motion, MR elastography. In another aspect, imaging systems may utilize a pulsed MRI system. For example, such systems may utilize a pre-polarized MRI so that the magnetic field is OFF during e-beam therapy delivery. In another aspect, such systems may utilize magnetic particle imaging could potentially image 'partially' using the fields that are already present due to beam steers means, such as bending magnets used to steer the high-energy e-beam. It is appreciated that some systems may incorporate any of the above aspects or combinations thereof in order to provide improved imaging capability.

In such embodiments, the magnetic-field based imaging systems may utilize gradients compatible with the particular radiation treatment system being used, RF coils, and other associated hardware: electron-beam compatible, or easily removable within a few seconds, or easy to integrate into the dose delivery plan, or completely out of the FOV and not affected by secondary radiation Ultrasound has the potential to be more broadly useful in the context of PHASER since use of very short life contrast agents, e.g. microbubbles, liposomal contrast agents etc. can be used rapidly, such as within a single breathhold, to provide real-time image guidance at the time of treatment. For example, 2D or 3D ultrasound with 3D real-time tracking (electro-magnetic, optical, infra-red etc.) may be used to provide precise positioning of the ultrasound images in real-time; images are acquired pre-treatment and registered within therapy treatment imaging frame of reference, followed by ultrasound imaging at the time of treatment for re-registration with prior 2D/3D images guided by updated ultrasound images. An ultrasound probe can be robot-mounted and computer controlled to provide images during therapy, and to ensure reproducibility of probe path, pressure and resulting soft-tissue deformation between pre-treatment ultrasound imaging and intra-therapy ultrasound imaging. In some embodiments, the robotic environment could include a HIFU probe for high-intensity focused ultrasound delivery to ablate as well as providing, via hyperthermia, short-term increase in blood flow and cellular activity so as to enhance the effect of the electron beam therapy. Ultrasound images may consist of: ultrasound imaging at standard MHz and higher frequencies depending on depth of tumor; harmonic imaging; correlation-enhanced ultrasound for reduced speckle. Ultrasound probes may be intra-cavity (e.g. esophageal), intravascular, or external.

Any of the above-listed (and some of the below-listed) imaging techniques sometimes may use contrast agents to enhance visibility of target structures. Use of contrast enhanced techniques may include use of: long-dwell-time vascular contrast agents; standard contrast agents; targeted contrast agents for delineation of target including tumor, atherosclerotic plaque etc.; and dose-enhancing agents, either transient or slow-uptake. For transient dose-enhancing agents, image-based triggering of dose delivery to the time of maximum agent uptake in target tissue may be implemented.

In another aspect, images of the anatomical structure to be treated may be processed to determine anticipated geography of the anatomical structure at time of treatment. Image processing may include a number of different techniques, which may include: segmentation—automatic or semi-automatic—of tissue, bone, lesion, metal, or organs at risk;

registration to previous 2D and 3D imaging modalities used for treatment planning and verification; and near-real-time iterative reconstruction of all imaging modalities.

In some embodiments, various motion management and motion tracking tools may incorporated into the imagining system. In contrast to conventionals systems, because dose delivery will be very fast, tracking does not apply to the interval 'during' therapy delivery, but rather to the interval just before therapy delivery and/or during acquisition of the pre-treatment images for determining treatment plans.

In one aspect, to control or verify dosage delivery, ECG-gated dose delivery may be provided according to any of the following aspects: (i) delivery of one pulse (ie. dose from a single nozzle, or multiple nozzles) per cardiac cycle, assuming reproducibility of cardiac motion; (ii) Real-time ECG-gated imaging for verification of sub-mm vessel motion, tissue location and other pulsatile-flow-generated motion e.g. brain motion; and (iii) Real-time ECG-gated imaging for structural heart imaging and tracking of cardiac structures during therapy for gated dose delivery. In addition, verification of dose delivery may include any of (i) surface-location verification using range cameras (e.g. infrared, optical); (ii) patient motion tracking to sub-mm accuracy using surface fiducials and standard tracking techniques; and (iii) continuous real-time imaging up to the moment of treatment with fine adjustment of final treatment geometry 2. Category 2: Patient Dose Delivery Verification In certain embodiments, the imaging system may include various means to verify delivery of the patient dose. Such means may include, but are not limited to, the following aspects: Fluorescence, bioluminescence, Cerenkov, near-infrared (skin blood perfusion) from patient surface during treatment, with/without appropriate contrast agents. Examples of the means by which dose delivery may be verified may include any of: (i) Detecting natural visible/near-infrared produced from patient surface during irradiation; (ii) Applying an agent (paint) to patient skin surface to enhance fluorescence/bioluminescence effect; (iii) Injecting an agent to enhance fluorescence/bioluminescence; and (iv) Inserting detectors (esophageal, rectal) to detect local signal, or any combination thereof. In some embodiments, the various cameras/detectors may be used to determine/quantify and/or verify delivery of the dose. The cameras/detectors used should be compatible with the applicable treatment environment.

In another aspect, the imaging systems may utilizing electron and/or acoustic imaging to monitor and/or verify dosage delivery. Such systems may include 2D or 3D (CT) acoustic imaging of deposited energy when a full dose (or fractional dose) is delivered in a very short time window with multiple short pulses and may be particularly useful when used in combination with fiducial markers with density that differs significantly from surrounding tissue. These systems may further include use of Compton Back-scatter/forward scatter detection from the patient during treatment.

In yet another aspect, imaging systems may be configured to include detection of other induced radiation during the energy-loss cascade. For examples, such configurations may include any of the following aspects: spectrum-specific detection of bursts of x-ray fluorescence from the cascade of secondary events as the electrons pass through the patient; enhanced by presence of high-Z materials such as high-Z contrast agents, fiducials; and spectroscopic approach utilizing a fast, energy-discriminating spectral detector eg. Ge, that is also robust to Brehmstrahlung irradiation.

3. Category 3: Entrance and Exit Beam Properties and Geometry

In accordance with certain embodiments, the imaging system may include any of various means for measuring beam geometry and properties at the entrance and/or exit of the beam. Examples of means that may be utilized in imaging systems in this category include features that allow measurement aspect of beam geometry and/or measurement of the beam energy profile. Measurement of beam geometry may be accomplished by any of: (i) exposure of single-use screen-film combination at entrance and exit ports of the electron beam; (ii) a Re-usable fluorescent screen with appropriate mirror/camera geometry e.g. CCD camera; and (iii) Direct irradiation of a pixellated detector with radiation-hard electronics for immediate readout. Measurement of beam energy profile may accomplished by use of a magnetic spectrometer for verification of energy spectrum or by measurement of Optical Transition Radiation for evaluation of beam energy deviation.

D. Unique Possibilities with Extremely Rapid Treatment Delivery and/or Very High-Energy Electron Therapy In certain aspects, real-time planning or adaptive planning may be enabled by: (1) Performing a therapy planning process to generate a plurality of therapy plans based on a diagnostic quality image of a subject and one or more foreseeable changes in the targeted tissue, in which the most suitable treatment plan may be identified utilizing smart search algorithms such as dynamic programming to efficiently sweep through the options, although other methods may be realized: or (2) Near real-time replanning of the original treatment plan utilizing cloud computing, GPU based computing and other fast computational methods that would allow near instantaneous, re-segmentation and dose calculation based on the diagnostic quality images obtained prior to treatment. In either case, the therapy session may utilize the treatment plan most suitable during that particular imaging session.

Figure 11A:
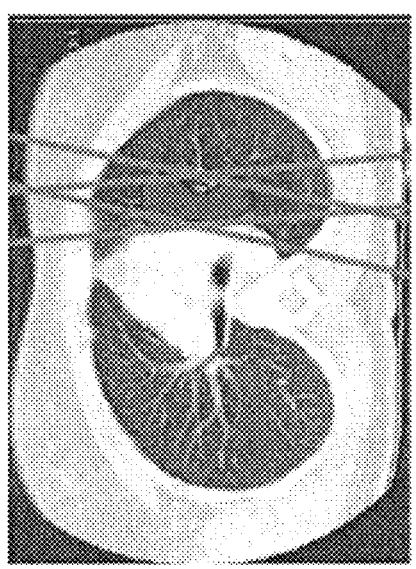
FIGS. 11A-11C illustrate treatment plans determined for multiple images of a target tissue of an organ for use in a rapid radiation treatment system.
Figure 11B:
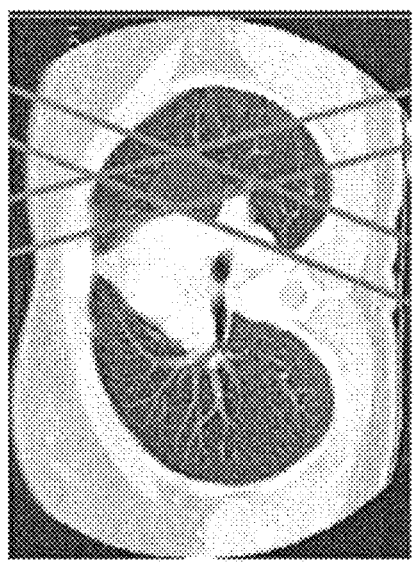
Figure 11C:
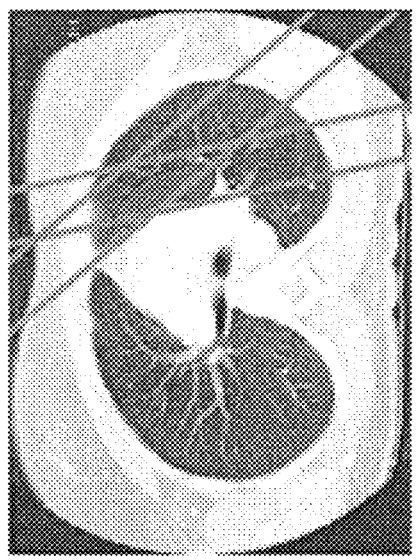
Figure 12A:
FIGS. 12A-12C illustrate detail views of the shape of the targeted organ in FIGS. 11A-11C imaged at different times in rapid succession.
Figure 12B:
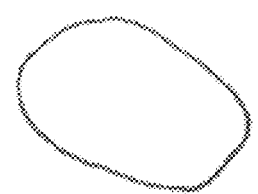
Figure 12C:

To further demonstrate the aspects relating to a plurality of treatment plan images described above, reference is made to FIGS. 11A-C and 12A-C. As shown in FIGS. 12A-C, the shape of a targeted tissue/organ may change considerably in images obtained over a relatively short period of time. This change in shape presents challenges in delivering highly targeted delivery of radiation within a sub-second timescale. In some cases, the tissue or organ changes shape in a cyclical manner such the organ is likely to return to a similar shape. In such cases, the imaging system may determine the most likely shape of the tissue from an image immediately preceding treatment. Although this method may utilize motion tracking or motion prediction, such methods need not rely on a predicted motion trajectory, but can predict the shape and/or location of the tissue from an immediately preceding shape and/or location based on past period motion. In other cases, the shape of the tissue depends on a variety of other factors, which may or may not be repeatable during the procedure. Nonetheless, in such cases, the shape of the organ is generally limited to a range of shapes within a particular volume and range of locations, which can be accounted for using various imaging programs or planning algorithms.

In accordance with some embodiments, a treatment plan can be devised for each of a plurality of images such that whichever treatment plan image the targeted tissue corresponds to at time of treatment is selected. This aspect is illustrated in FIGS. 11A-11C, which depict differing angles and projection paths of the radiation treatment beams to deliver the desired radiation dose to the targeted tissue. The differing shapes and locations of the anatomical structure having the targeted tissue are shown in FIGS. 12A-12C.

Upon time of treatment, the treatment image most closely corresponding with the real-time image of the targeted tissue is selected for delivery of the radiation treatment. In another aspect, the imaging system may calculate a shape between shapes of two consecutive pretreatment images, such as between the shapes in FIGS. 12A and 12B. such that the system can determine a predicted shape and/or location of the structure in a period of time between consecutive shapes of the pretreatment images. In another aspect, when delivery of the radiation dose is sufficiently fast to freeze physiologic motion, the real-time imaging may be configured to trigger delivery of the dose, such that when the organ returns to or moves into a shape and/or location of the pre-treatment images, the dose is delivered to the targeted tissue according to the pre-determined treatment plan associated with the shape and/or location of that image or the immediately subsequent image.

In one aspect, the imaging embodiments described above are particularly advantageous when applied to rapid radiation therapies by allowing for fast imaging, fast re-planning and fast delivery of the intended radiation dose to the targeted tissue, such as along the time-scales of rapid radiation treatments described herein. As such imaging, replanning and dose delivery can occur in a considerably reduced time-frame as compared to conventional treatment methods, such as a time-frame of a single breath-hold. Another advantage resides in providing more accurate radiation therapy plans for fractionated and hypo-fractionated radiation therapy. Other advantages include computationally efficient predictive adaptation of the radiation therapy plan to foreseeable changes in the targeted tissue and other organs.

In another aspect, any of the imaging features described above can be configured for use in timing of radiation with pharmacokinetics of radiation modifying drugs (chemo, sensitizers, protectors, etc.) so as to synchronize with the maximum tumor: normal tissue differential.

As a non-limiting example, very rapid imaging may be provided by a full ring integrated CT imaging system. Using such a system, a workflow capitalizing on the present invention's unique capabilities may comprise the following steps: 1. An initial simulation prior to treatment used to produce a plurality of plans optimized for a variety of anticipated anatomical variations; 2. At the time of treatment, acquire a high-quality 3-D acquisition covering the entire treatment volume of targeted tissue and surrounding tissue that may be traversed by the radiation beams; 3. Automatic or semi-automatic re-segmentation (e.g., through deformable image registration) of anatomic structures and recalculation or selection from precalculated validated plans; 4. Operator verification of the automatic segmentation and plan choices; 5. Rapid (approximately 1 second) image acquisition for verification within e.g. a breath hold and extremely rapid comparison (eg by subtraction or registration) in order to select the final plan automatically from a restricted set of options determined in step 3. Additional time reduction may be achieved by dynamic updating of the reconstruction during data acquisition until convergence is obtained on the optimal plan choice; and 6. Rapid treatment delivery. Steps 5-6 would be automatic according to a desired treatment on a time scale faster than physiologic motion.

E. General

Numerous specific details are set forth herein to provide a thorough understanding of the claimed subject matter. However, those skilled in the art will understand that the claimed subject matter may be practiced without these specific details. In other instances, methods, apparatuses or systems that would be known by one of ordinary skill have not been described in detail so as not to obscure subject matter that may be claimed.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed is:

1. An imaging system for image verification in a high-energy rapid radiation delivery treatment system configured to deliver an entire conformal 3D dose for a given radiation treatment session in less than 10 seconds, wherein high-energy comprises 1-250 MeV and the entire dose is at least 1 Gy, the system comprising:
   an imaging device configured for obtaining a 3D treatment image of an anatomical structure that includes the targeted tissue to which the treatment is to be delivered; and
   a processing unit having a recordable memory with a plurality of predetermined 3D treatment plans recorded thereon, the plurality of predetermined treatment plans determined from a plurality of pre-treatment images, the processing unit being configured to:
   determine a shape and/or location of the anatomical structure at treatment based on the treatment image and the plurality of pre-treatment images; and
   determine a single actual conformal 3D treatment pattern suitable for delivery from which the entire conformal 3D dose is delivered to the targeted tissue, wherein the single conformal 3D treatment pattern is determined based on the determined shape and/or location of the anatomical structure and one or more of the plurality of predetermined treatment plans,
   wherein the imaging device is operably coupled to the rapid radiation delivery treatment system.

2. The system of claim 1 wherein the actual treatment pattern is a plurality of actual treatment patterns each associated with a different direction of the plurality of differing directions from where a plurality particle beams from a treatment system are delivered to the targeted tissue.

3. The system of claim 1 wherein
   the imaging system is configured to perform a re-planning process, wherein the re-planning process comprises:
   obtaining a plurality of images in rapid succession immediately before treatment, and
   configured to alter the plurality of predetermined treatment plans based on the plurality of images obtained immediately before treatment, wherein the re-planning process is performed in less than 20 seconds.

4. The imaging system of claim 1 wherein the processing unit is further configured to:
   determine the actual treatment plan by:
   selecting one of the predetermined treatment plans, and
   adapting the selected predetermined treatment plans based on the treatment image.

5. The imaging system of claim 1 wherein the imaging device includes any of CT, MR, PET, SPECT and ultrasound imaging or any combination thereof.

6. The imaging system of claim 1 wherein the imaging system comprises a full ring integrated CT imaging system.

7. The imaging system of claim 1 wherein the processing unit is further configured to:
perform an initial simulation prior to treatment to determine the plurality of predetermined treatment plans based on a plurality of anticipated anatomical variations.

8. The imaging system of claim 7 wherein the processing unit is further configured to:
perform rapid image acquisition to obtain the treatment image in about 1 second or less for verification and perform rapid comparison of the treatment image with one of the plurality of pre-treatment images by subtraction or registration to determine the actual treatment plan.

9. The imaging system of claim 7 wherein the one or more pretreatment plans comprise a 3D reconstruction of the anatomical structure and the processing unit is further configured to determine the actual treatment pattern by dynamically updating the 3D reconstruction during data acquisition so as to optimize the treatment pattern.

10. The imaging system of claim 1 wherein the treatment image is a high-quality 3D image covering an entire treatment volume of the targeted tissue to be traversed by a plurality of treatment beams directed to the targeted tissue from multiple directions.

11. The imaging system of claim 1 wherein the predetermined treatment plan includes a segmentation of anatomic structures and the processing unit is further configured to:
perform an automatic or semi-automatic re-segmentation of anatomic structures and recalculation of or selection of a plurality of pre-calculated validated plans.

12. The system of claim 1, wherein the treatment system is configured for electron therapy or photon therapy.

13. The system of claim 1, wherein the treatment image is a "real-time" image such that the single treatment plan is based on the "real-time" image at treatment delivery.

14. A high-energy treatment system for delivering a rapid radiation treatment to a patient, wherein high-energy comprises 1-250 MeV, the system comprising:
a plurality of accelerating structures configured to rapidly deliver a plurality of particle beams to the targeted tissue of a patient from a plurality of differing directions such that an entire dose of the radiation treatment for the treatment session is delivered to the targeted tissue in less than 10 seconds;
an imaging system in accordance with claim 1; and
a control unit operatively coupling the plurality of accelerating structures to the imaging system, wherein the control unit is configured to deliver the plurality of beams to the targeted tissue according to the actual treatment pattern determined by the imaging system.

15. A method for treating a tissue of a patient, said method comprising:
obtaining a 3D treatment image of an anatomical structure of the patient with an imaging system, the anatomical structure including a tissue targeted for treatment;
determining a shape and/or location of the anatomical structure at treatment based on the treatment image and a plurality of pre-treatment images obtained prior to obtaining the treatment image;
determining a single actual 3D conformal treatment plan for the targeted tissue based on the treatment image and a treatment plans determined from the plurality of pre-treatment images; and
delivering an entire 3D conformal dose of a radiation treatment to the targeted tissue for a given treatment session with a high-energy rapid radiation treatment system, wherein the entire 3D conformal dose is delivered according to the single actual treatment plan in less than 10 seconds, wherein high-energy comprises 1-250 MeV and the entire dose is at least 1 Gy.

16. The method of 15 wherein the determined shape and/or location of the anatomical structure at treatment corresponds to a particular pre-treatment image when the treatment image corresponds to another image of the plurality of pre-treatment images immediately preceding the particular pre-treatment image.

17. The method of claim 15 wherein determining the shape and/or location comprises performing a segmentation of the plurality of pre-treatment images and wherein determining the actual treatment plan includes performing a rapid re-segmentation of the treatment image and dose calculation according to the determined shape and/or location of the anatomical structure immediately before treatment.

18. The method of claim 15 wherein obtaining the treatment image comprises obtaining a full CT scan.

19. The method of claim 18 further comprising:
performing registration with the full CT scan, wherein the full CT scan and registration is performed within about one second or less.

20. The method of claim 15 wherein obtaining the treatment image comprises:
detuning a linear accelerator of a treatment system through which one or more electron beams are accelerated for delivering a radiation treatment;
detuning the linear accelerator to generate an electron beam of lower energy than those of the one or more electron beams for treatment; and
directing the lower-energy electrons to a high-Z target so as to produce a diagnostic energy spectrum suitable for imaging of the targeted tissue with the same linear accelerator as is used for acceleration of the one or more treatment beams.

21. The method of claim 20 further comprising any of:
determining a treatment plan based on a diagnostic image obtained using the lower-energy electron beam;
tuning the linear accelerator so as to provide a higher energy electron beam suitable for treatment after obtaining the diagnostic image; and
performing detuning and tuning of the linear accelerator sufficiently rapidly so as to obtain the diagnostic image, determine the treatment plan and deliver an entire treatment dose based on the determined treatment plan in less than one minute.

22. The method of claim 15, wherein the treatment comprises electron therapy or photon therapy.

23. The method of claim 15, wherein the treatment image is a "real-time" image such that the single treatment plan is based on the "real-time" image at treatment delivery.

24. A method of performing a high-energy, rapid radiation treatment with a delivery treatment system configured to deliver an entire 3D conformal dose for a given radiation treatment session to a targeted tissue in less than 10 seconds, wherein high energy comprises 1-250 MeV and the entire dose is at least 1 Gy, the method comprising:
performing an initial simulation prior to treatment so as to produce a plurality of treatment plans before treatment optimized for differing anticipated anatomical variations, wherein the treatment plans comprise a segmentation of anatomical structures that include the targeted tissue;

at the time of treatment, acquire a diagnostic image covering the entire treatment volume of the targeted tissue and surrounding tissue that may be traversed by one or more radiation treatment beams;

performing re-segmentation of anatomical structures of the diagnostic image and recalculation or selection of treatment plan options from one or more of the treatment plans produced before treatment;

verifying segmentation and selection of treatment plan options;

rapidly obtaining a treatment image and verifying selection of a single treatment plan from the plurality of treatment plan options within about one second or less; and rapidly delivering a high-energy radiation treatment beam according to the determined and verified selected treatment plan, wherein an entire dose of the treatment is delivered within 10 seconds or less in accordance with the single treatment plan.

25. The method of claim 24 wherein the one or more treatment plans comprise a 3D reconstruction of anatomical structure, the method further comprising:

dynamically updating the 3D reconstruction from the diagnostic image acquired at the time of treatment to obtain an optimal plan choice and the selected treatment plan.

26. The method of claim 24 wherein any of:

re-segmentation is performed through deformable image registration;

re-segmentation is automatic or semi-automatic so as to be performed in less than 10 seconds;

obtaining the diagnostic image comprises obtaining a full CT scan;

verification segmentation and treatment plan selection comprises automated or semi-automated rapid image comparison utilizing subtraction and/or registration; and the entire process is performed in about 20 seconds or less and treatment is delivered in about one second or less.

27. The method of claim 24, wherein the treatment comprises electron therapy or photon therapy.

28. The method of claim 24, wherein the treatment image is a "real-time" image such that the single treatment plan is based on the "real-time" image at treatment delivery.

* * * * *

UNITED STATES PATENT AND TRADEMARK OFFICE
CERTIFICATE OF CORRECTION

| | | |
|---|---|---|
| PATENT NO. | : 10,806,950 B2 | Page 1 of 1 |
| APPLICATION NO. | : 15/944670 | |
| DATED | : October 20, 2020 | |
| INVENTOR(S) | : Rebecca Fahrig et al. | |

It is certified that error appears in the above-identified patent and that said Letters Patent is hereby corrected as shown below:

In the Specification

Column 1, Line 23 please insert:
--STATEMENT OF GOVERNMENT SPONSORED SUPPORT
This invention was made with Government support under contract DE-AC02-76SF00515 awarded by the Department of Energy. The Government has certain rights in the invention.--

Signed and Sealed this
Seventh Day of May, 2024

Katherine Kelly Vidal
*Director of the United States Patent and Trademark Office*